United States Patent
Kaplan

(10) Patent No.: US 9,381,173 B2
(45) Date of Patent: Jul. 5, 2016

(54) ISOLATED STEREOISOMERIC FORMS OF (S)2-N(3-O-(PROPAN 2-OL)-1-PROPYL-4-HYDROXYBENZENE)-3-PHENYLPROPYLAMIDE

(71) Applicant: Novaremed Ltd., Petah Tiqwa (IL)

(72) Inventor: Eliahu Kaplan, Petach Tiqwa (IL)

(73) Assignee: Novaremed Ltd., Petah Tiqwa (IL)

( * ) Notice: Subject to any disclaimer, the term of this patent is extended or adjusted under 35 U.S.C. 154(b) by 0 days.

(21) Appl. No.: 14/291,901

(22) Filed: May 30, 2014

(65) Prior Publication Data

US 2014/0275270 A1    Sep. 18, 2014

Related U.S. Application Data

(63) Continuation of application No. PCT/IL2012/050512, filed on Dec. 6, 2012.

(60) Provisional application No. 61/568,219, filed on Dec. 8, 2011.

(51) Int. Cl.
*A61K 31/165* (2006.01)
*C07C 233/22* (2006.01)

(52) U.S. Cl.
CPC ............. *A61K 31/165* (2013.01); *C07C 233/22* (2013.01)

(58) Field of Classification Search
CPC ............................ C07C 233/22; A61K 31/165
See application file for complete search history.

(56) References Cited

U.S. PATENT DOCUMENTS

| | | | |
|---|---|---|---|
| 7,642,290 B2 | 1/2010 | Kaplan | |
| 7,674,829 B2 * | 3/2010 | Kaplan | ............... A61K 31/165 514/617 |
| 7,754,771 B2 | 7/2010 | Kaplan | |
| 2006/0148874 A1 * | 7/2006 | Kaplan et al. | ................ 514/396 |
| 2011/0086910 A1 | 4/2011 | Kaplan | |

FOREIGN PATENT DOCUMENTS

| | | | | |
|---|---|---|---|---|
| IL | WO 2009109850 A2 * | 9/2009 | ........... A61K 31/165 |
| WO | WO2005/092305 A2 * | 10/2005 | |
| WO | 2009109850 A2 | 9/2009 | |
| WO | 2011030205 A1 | 3/2011 | |

OTHER PUBLICATIONS

Tsuda et al., (2008) Lyn tyrosine kinase is required for P2X(4) receptor upregulation and neuropathic pain after peripheral nerve injury. Glia 56(1): 50-8.

\* cited by examiner

*Primary Examiner* — Nyeemah A Grazier
*Assistant Examiner* — Amanda L Aguirre
(74) *Attorney, Agent, or Firm* — The Roy Gross Law Firm, LLC; Roy Gross

(57) ABSTRACT

Isolated stereoisomeric forms of the compound (S)2-N(3-O-(propan 2-ol) -1-propyl-4-hydroxybenzene)-3-phenylpropylamide and uses in the treatment of pain.

17 Claims, 6 Drawing Sheets

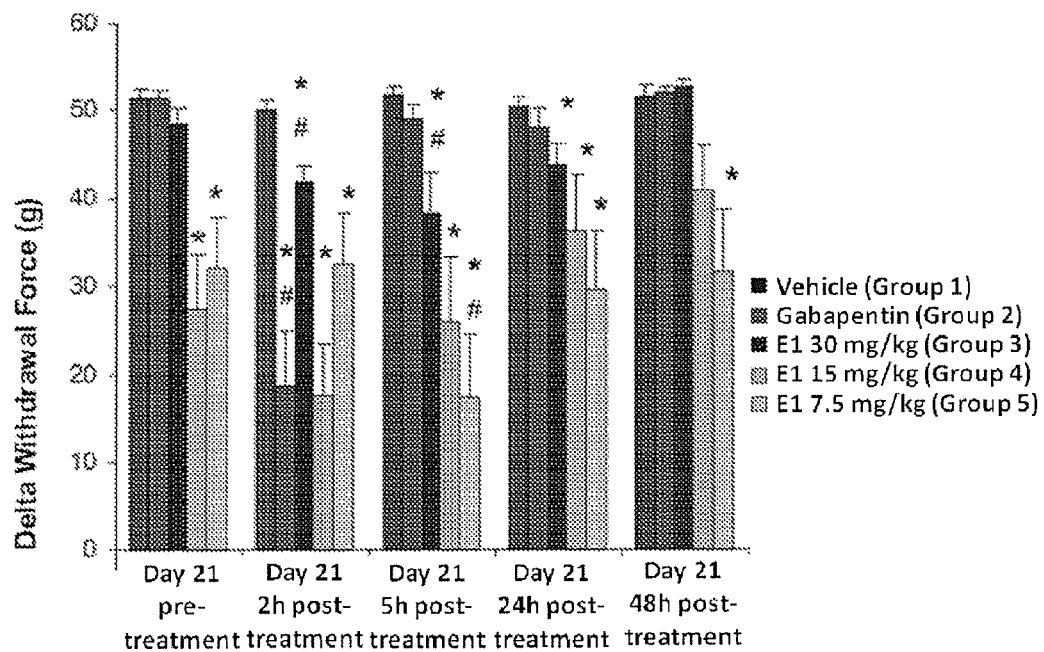
Figure 5B
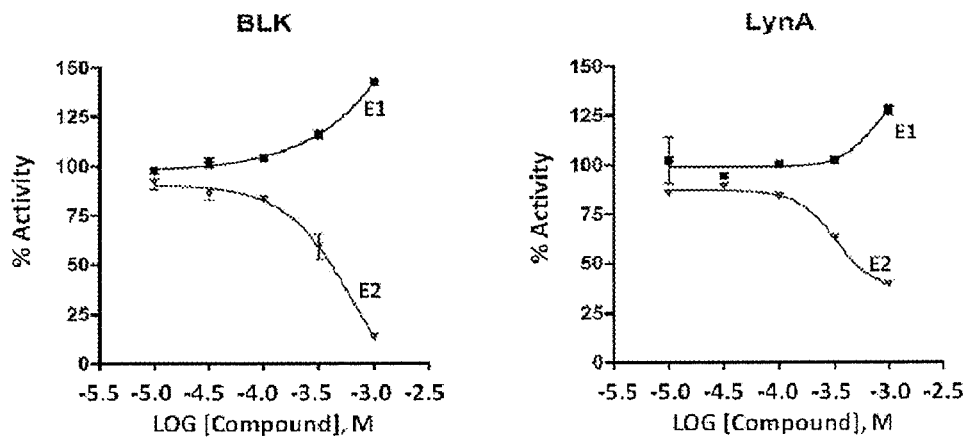
Figure 6A
Figure 6B

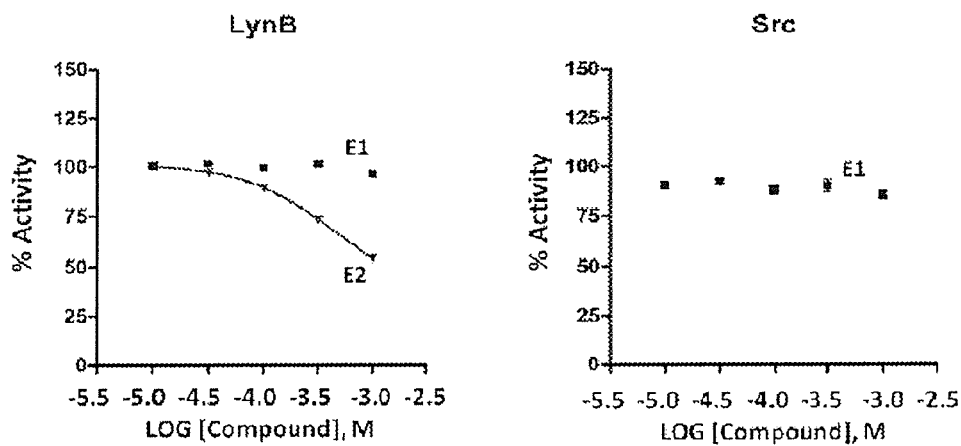
Figure 6C
Figure 6D
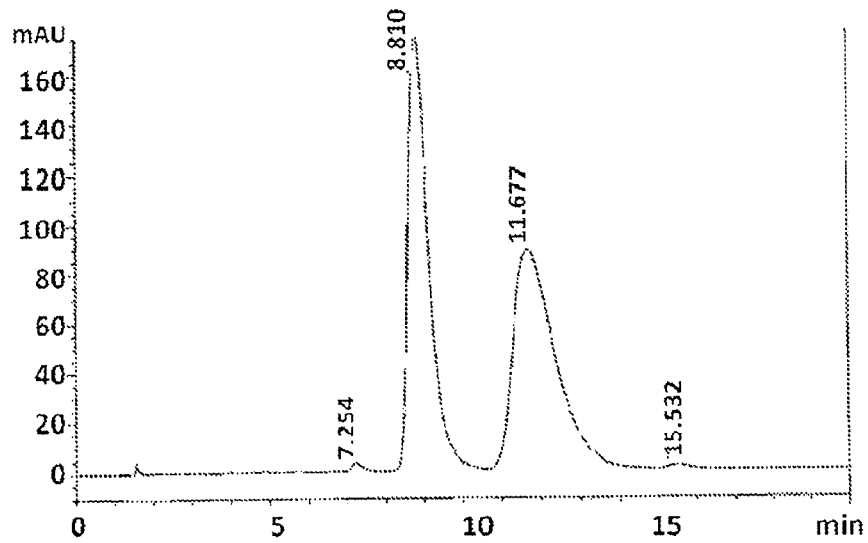
Figure 7A

ISOLATED STEREOISOMERIC FORMS OF (S)2-N(3-O-(PROPAN 2-OL)-1-PROPYL-4-HYDROXYBENZENE)-3-PHENYLPROPYLAMIDE

FIELD OF THE INVENTION

The present invention relates to isolated stereoisomeric forms of the compound (S)2-N(3-O-(propan 2-ol)-1-propyl-4-hydroxybenzene)-3-phenylpropylamide. Specifically, the present invention relates to the use of (S)2-N(3-O—((S)propan 2-ol)-1-propyl-4-hydroxybenzene)-3-phenylpropylamide in the treatment or prophylaxis of pain, in particular, neuropathic pain.

BACKGROUND OF THE INVENTION

The compound 2-N(3-O-(propan 2-ol)-1-propyl-4-hydroxybenzene)-3-phenylpropylamide is disclosed in U.S. Pat. No. 7,754,771, and has proven to be efficient in the treatment of HIV-1 infection. This compound has been further disclosed for use in the treatment or prophylaxis of pain and inflammation in WO 2009/1099850, WO 2011/030105 and US 2011/0086910. Previous disclosures on this compound have related to the racemate containing all four enantiomers and diastereomers, namely (S,S), (S,R), (R,R) and (R,S). The racemate containing the S enantiomers at the chiral position adjacent to the amide, were disclosed as a particularly advantageous embodiment.

Pain is a multifaceted or multidimensional, experiential response to a variety of stimulus conditions. Pain is defined by the International Association for the Study of Pain (IASP) as "an unpleasant sensory and emotional experience associated with actual or potential tissue damage, or described in terms of such damage".

Pain can be acute or chronic. Acute pain is usually caused by soft tissue damage, infection and/or inflammation among other causes. Chronic pain may have no apparent cause or may be caused by a developing illness or imbalance. Chronic pain is defined as the disease of pain; its origin, duration, intensity and specific symptoms may vary. Moreover, chronic pain can be classified as either nociceptive or neuropathic. Nociceptive pain includes tissue injury-induced pain and inflammatory pain such as that associated with arthritis. Nociceptive pain has been traditionally managed by administering non-opioid analgesics, such as acetylsalicylic acid, choline magnesium trisalicylate, acetaminophen, ibuprofen, fenoprofen, diflusinal, and naproxen; or opioid analgesics, including morphine, hydromorphone, methadone, levorphanol, fentanyl, oxycodone, and oxymorphone. Neuropathic pain, a debilitating chronic pain following nerve damage, is characterized by its chronic nature, hyperalgesia, or abnormal pain hypersensitivity to innocuous stimuli (tactile allodynia). Hyperalgesia is an exaggerated response to a painful stimulus. Allodynia is the perception of normal stimuli as painful (examples include the touch of clothing, warm or cool air, etc.). Neuropathic pain can be a sequel to nerve damage in an extremity such as an arm, or more often, a leg. Precipitating events can include trauma or amputations (e.g., phantom limb pain). Neuropathic pain can occur due to an adverse effect of drug therapies, e.g., vincristine or paclitaxel (Taxol™), or can occur as a component of disease pathologies, such as diabetes type 1 or type 2, shingles, HIV-1 infections, etc. Typically, neuropathic pain does not respond to opiates or non-steroidal anti-inflammatory drugs such as aspirin. Current suggested medicaments to Neuropathic pain include anti-epileptics (e.g., gabapentin, carbamazepine, valproic acid, topiramate, phenyloin), NMDA antagonists (e.g., ketamine, dextromethorphan), topical lidocaine (for post-herpetic neuralgia), and tricyclic antidepressants (e.g., fluoxetine, sertraline and amitriptyline).

The underlying mechanisms of neuropathic pain are still to be determined. However, it has been recently suggested that Lyn tyrosine kinase, a member of the Src family kinases (SFKs) plays an important role in the pathogenesis of neuropathic pain. Lyn expression in the spinal cord was highly restricted to microglia, and its level was increased after nerve injury. It has been shown that mice lacking Lyn exhibit a striking reduction in their ability to tactile allodynia after nerve injury. It was concluded that neuropathic pain may be linked to up-regulation of Lyn tyrosine kinase. (See Tsuda et al., *Glia*, 2008, 56:50-8).

The currently available treatments for neuropathic pain have only low to moderate efficacy, and many patients are left without significant pain relief. The lack of adequate pain relief for millions of people with neuropathic pain, as well as for those with other types of pain, represents a great unmet medical need, this invention addresses that need.

SUMMARY OF THE INVENTION

The present invention relates to isolated stereoisomeric forms of the compound (S)2-N(3-O-(propan 2-ol)-1-propyl-4-hydroxybenzene)-3-phenylpropylamide of formula I.

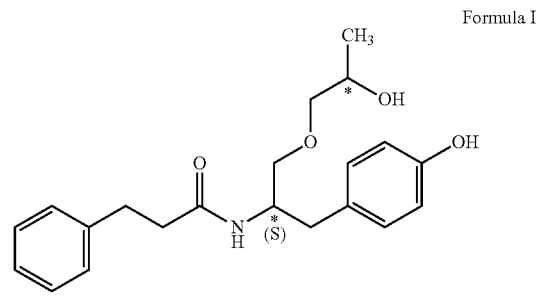

Formula I

Specifically the present invention relates to the isolated enantiomer (S)2-N(3-O—((S)propan 2-ol)-1-propyl-4-hydroxybenzene)-3-phenylpropylamide) for use in the treatment or prophylaxis of pain, in particular neuropathic pain.

The present invention is based in part on the surprising discovery that the substantially pure enantiomers (S)2-N(3-O—((S)propan 2-ol)-1-propyl-4-hydroxybenzene)-3-phenylpropylamide (also known as the (S,S) enantiomer or E1) and (S)2-N(3-O—((R)propan 2-ol)-1-propyl-4-hydroxybenzene)-3-phenylpropylamide (also known as the (S,R) enantiomer or E2) modulate the activity of specific tyrosine kinases in an opposite manner. It was unexpectedly found that while the (S,S) enantiomer activated protein tyrosine kinases LynA and BLK, the (S,R) enantiomer inhibited their activity. It was further unexpectedly shown that the (S,S) enantiomer was effective as a pain analgesic in animal models of pain, while the (S,R) enantiomer was shown to be ineffective or less effective in these models. Furthermore, the analgesic effect of the (S,S) enantiomer was long acting as it was efficacious for more than 24 hours post administration, in comparison to the commonly used analgesic agent gabapentin which was effective for no longer than 5 hours post administration.

According to a first aspect, the present invention provides a compound of formula II Formula II

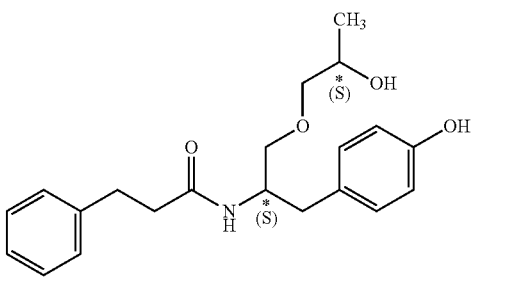

having the specific stereochemistry of (S)2-N(3-O—((S)propan 2-ol)-1-propyl-4-hydroxybenzene)-3-phenylpropylamide or a pharmaceutically acceptable salt or hydrate thereof in a substantially pure form.

According to a second aspect, the present invention provides a compound of formula III Formula III

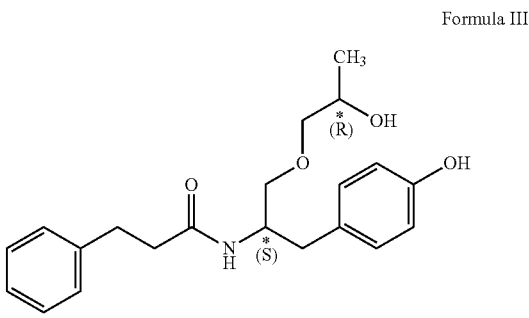

having a specific stereochemistry of (S)2-N(3-O—((R)propan 2-ol)-1-propyl-4-hydroxybenzene)-3-phenylpropylamide or a pharmaceutically acceptable salt or hydrate thereof in a substantially pure form.

As used herein and unless otherwise indicated, the term "substantially pure" when used to describe an enantiomer of a compound means that one enantiomer is substantially free of other stereoisomeric forms of the compound. A representative substantially pure enantiomer comprises greater than 90% by weight of one enantiomer of the compound and less than 10% by weight of the other stereoisomeric forms of the compound, preferably greater than 95% by weight of one enantiomer of the compound and less than 5% by weight of the other stereoisomeric forms of the compound, even more preferably greater than 98% by weight of one enantiomeric form of the compound and less than 2% by weight of the other stereoisomeric forms of the compound. As used herein "other stereoisomeric forms" may include at least one of the (S,S), (S,R), (R,S) and (R,R) enantiomeric or diastereomeric forms of the compound 2-N(3-O-(propan 2-ol)-1-propyl-4-hydroxybenzene)-3-phenylpropylamide.

According to some embodiments the substantially pure enantiomer of formula II ((S,S) enantiomer) is capable of activating BLK and LynA tyrosine kinases. According to other embodiments the substantially pure enantiomer of formula III (S,R enantiomer) is capable of inhibiting BLK and LynA tyrosine kinases. Surprisingly, the (S,S) enantiomer had no effect on the activity of LynB tyrosine kinase while the (S,R) enantiomer inhibited its activity.

According to a second aspect, the present invention provides a therapeutic agent for the treatment of pain, comprising an activator of BLK and/or LynA tyrosine kinases as the active ingredient. According to some embodiments, the pain is an acute pain. According to some other embodiments the pain is a chronic pain. According to some embodiments, the chronic pain is nociceptive pain. According to some currently preferred embodiments, the chronic pain is neuropathic pain. Each possibility represents a separate embodiment of the invention.

According to some embodiments, the activator of BLK and/or Lyn A tyrosine kinase is a substantially pure (S)2-N (3-O—((S)propan 2-ol)-1-propyl-4-hydroxybenzene)-3-phenylpropylamide or a pharmaceutically acceptable salt or hydrate thereof.

According to some embodiments, the neuropathic pain is at least one symptom selected from neuropathic pains in post herpetic neuralgia, trigeminal neuralgia, diabetic neuralgia, cancer pain, persistent postoperative or post-traumatic pain, hyperalgia, allodynia, post-thoracotomy pain, CRPS, pain associated with multiple sclerosis, AIDS, thalamic pain, paraplegic pain caused by myelopathy, anesthesia dolorosa and phantom limb pain.

According to a third aspect, the present invention provides a pharmaceutical composition comprising an activator of BLK and/or LynA tyrosine kinases as an active ingredient. Each possibility represents a separate embodiment of the invention. According to some embodiments, the pharmaceutical composition comprises a substantially pure (S)2-N(3-O—((S)propan 2-ol)-1-propyl-4-hydroxybenzene)-3-phenylpropylamide or a pharmaceutically acceptable salt or hydrate thereof and a pharmaceutically acceptable carrier or diluent. According to some embodiments, the pharmaceutical composition is useful for the treatment of pain. According to some embodiments, the pain may be acute or chronic.

According to some further embodiments, the chronic pain may be nociceptive pain or neuropathic pain.

According to some embodiments, the pharmaceutical composition is formulated as a unit dosage form. According to some embodiments, the unit dosage comprises from 0.1 to 500 mg of substantially pure (S)2-N(3-O—((S)propan 2-ol)-1-propyl-4-hydroxybenzene)-3-phenylpropylamide or a pharmaceutically acceptable salt or hydrate thereof. According to some embodiments, the pharmaceutical composition is formulated for oral administration.

According to a further aspect, the present invention provides methods for the treatment or prophylaxis of pain in a subject in need thereof, comprising administering to the subject a pharmaceutical composition comprising as an active ingredient a compound comprising substantially pure (S)2-N (3-O—((S)propan 2-ol)-1-propyl-4-hydroxybenzene)-3-phenylpropylamide or a pharmaceutically acceptable salt or hydrate thereof. According to some embodiments, the methods of the present invention comprise administering a daily dose of 1.0 mg to 15 g of the active ingredient. According to specific embodiments the methods of the invention provide analgesia over a period of 24 hours after a single administration of the pharmaceutical composition.

The present invention further relates to the use of substantially pure (S)2-N(3-O—((S)propan 2-ol)-1-propyl-4-hydroxybenzene)-3-phenylpropylamide or a pharmaceutically acceptable salt or hydrate thereof for the preparation of a medicament for the treatment or prophylaxis of pain. According to some embodiments the pain is neuropathic pain. According to specific embodiments the methods of the invention provide analgesia over a period of 24 hours after a single administration of the pharmaceutical composition.

The present invention will be more fully understood from the following figures and detailed description of the preferred embodiments thereof.

BRIEF DESCRIPTION OF THE DRAWINGS

FIGS. 5A-5B show the difference (delta) force between right healthy leg and left operated leg measured on the $14^{th}$ day of the study 2, 5 and 24 hours post treatment and on the $21^{st}$ day of the study 2, 5, 24 and 48 hours post treatment. Study groups from left to right include: vehicle (group 1); Gabapentin (group 2); 30 mg/kg of substantially pure (S)2-N(3-O—((S)propan 2-ol)-1-propyl-4-hydroxybenzene)-3-phenylpropylamide (group 3); 15 mg/kg of substantially pure (S)2-N(3-O—((S)propan 2-ol)-1-propyl-4-hydroxybenzene)-3-phenylpropylamide (group 4); 7.5 mg/kg of substantially pure (S)2-N(3-O—((S)propan 2-ol)-1-propyl-4-hydroxybenzene)-3-phenylpropylamide (group 5). * $p<0.05$ vs. Vehicle #$p<0.05$ Pretreatment vs. Post-treatment.

FIGS. 6A-6D show the modulation the protein tyrosine kinases, BLK, LynA, LynB and Src by the compounds of the invention, presented in the form of $IC_{50}$ and $EC_{50}$ curves.

FIGS. 7A-7C show the chiral separation of (S)2-N(3-O—((S)propan 2-ol)-1-propyl-4-hydroxybenzene)-3-phenylpropylamide and (S)2-N(3-O—((R)propan 2-ol)-1-propyl-4-hydroxybenzene)-3-phenylpropylamide using a supercritical fluid chromatography (SFC) in combination with chiral stationary phases. A: racemate of E1 and E2 enantiomers; B: substantially pure E1 enantiomer; C: substantially pure E2 enantiomer.

DETAILED DESCRIPTION

The present invention relates to isolated stereoisomeric forms of the compound (S)2-N(3-O-(propan 2-ol)-1-propyl-4-hydroxybenzene)-3-phenylpropylamide and to uses thereof for the therapeutic modulation of kinase-mediated processes, and treatment of disease and disease symptoms, particularly those mediated by certain kinase enzymes. Specifically, the present invention related to the use of substantially pure (S)2-N(3-O—((S)propan 2-ol)-1-propyl-4-hydroxybenzene)-3-phenylpropylamide in the treatment of pain, preferably neuropathic pain.

As used herein and unless otherwise indicated, the term "substantially pure" when used to describe an enantiomer of a compound means that one enantiomer is substantially free of other stereoisomeric forms of the compound. A representative substantially pure enantiomer comprises greater than about 80% by weight of one enantiomer of the compound and less than about 20% by weight of other stereoisomeric forms of the compound, preferably greater than about 85% by weight of one enantiomer of the compound and less than about 15% by weight of other stereoisomeric forms of the compound, preferably greater than about 90% by weight of one enantiomer of the compound and less than about 10% by weight of the other stereoisomeric forms of the compound, more preferably greater than about 95% by weight of one enantiomer of the compound and less than about 5% by weight of the other stereoisomeric forms of the compound, more preferably greater than about 96% by weight of one enantiomer of the compound and less than about 4% by weight of the other stereoisomeric forms of the compound, even more preferably greater than about 97% by weight of one enantiomeric form of the compound and less than about 3% by weight of the other stereoisomeric forms of the compound, even more preferably greater than about 98% by weight of one enantiomeric form of the compound and less than about 2% by weight of the other stereoisomeric forms of the compound and most preferably greater than about 99% by weight of one enantiomeric forms of the compound and less than about 1% by weight of the other stereoisomeric forms of the compound. As used herein "other stereoisomeric forms" may include at least one of the (S,S), (S,R), (R,S) and (R,R) enantiomeric or diastereomeric forms of the compound 2-N (3-O-(propan 2-ol)-1-propyl-4-hydroxybenzene)-3-phenylpropylamide.

The term "about" as used herein denotes at most ±10% of the value indicated, preferably no more than ±5%.

Figure 7B:
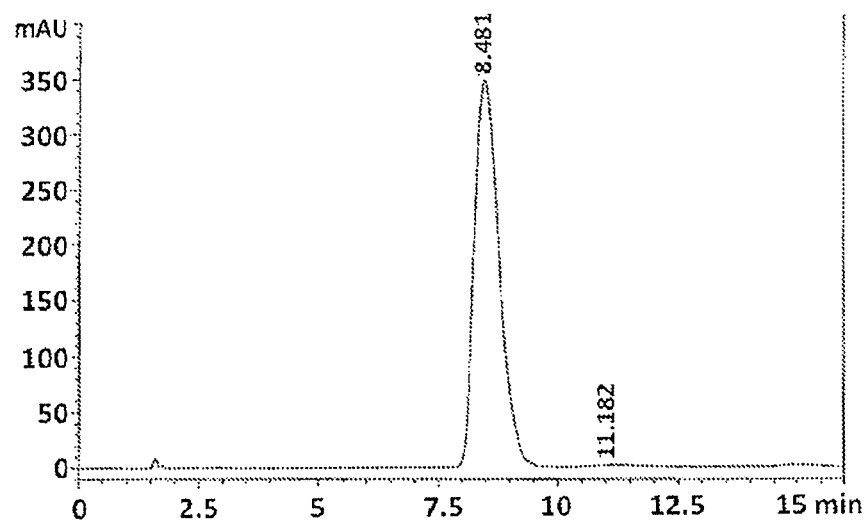
Figure 7C:
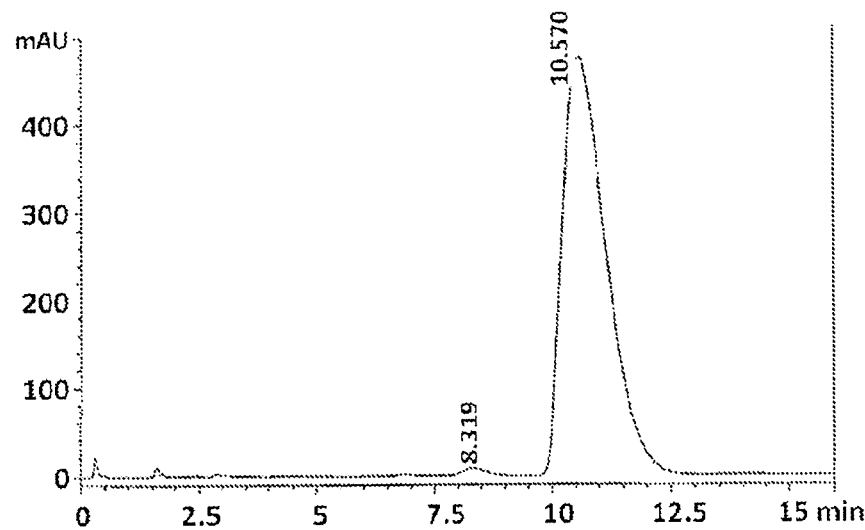

The isolated enantiomers according to some embodiments of the invention may be synthesized as a racemate by known in the art methods described for example in U.S. Pat. Nos. 7,754,771, 7,642,290, 7,674,829 or US 2011/0086910. The racemate may be further separated by known in the art methods for the separation of chiral compounds. According to an exemplary embodiment, the enantiomers may be synthesized as a racemate (comprising (S)2-N(3-O—((S)propan 2-ol)-1-propyl-4-hydroxybenzene)-3-phenylpropylamide and (S)2-N(3-O—((R)propan 2-ol)-1-propyl-4-hydroxybenzene)-3-phenylpropylamide and be further separated by a supercritical fluid chromatography (SFC) in combination with chiral stationary phases. Specifically, the (S,S) and (S,R) compounds may be separated on RegisPack™ column a polysaccharide coated chiral column (with a tris-(3,5-dimethylphenyl) carbamoyl cellulose selector) generally used for enantiomeric separations of a wide range of racemate classes (FIG. 7A-C).

According to some embodiments, the enantiomers may be synthesized directly using for example, the process described in scheme 1 for the preparation of the (S,S) enantiomer.

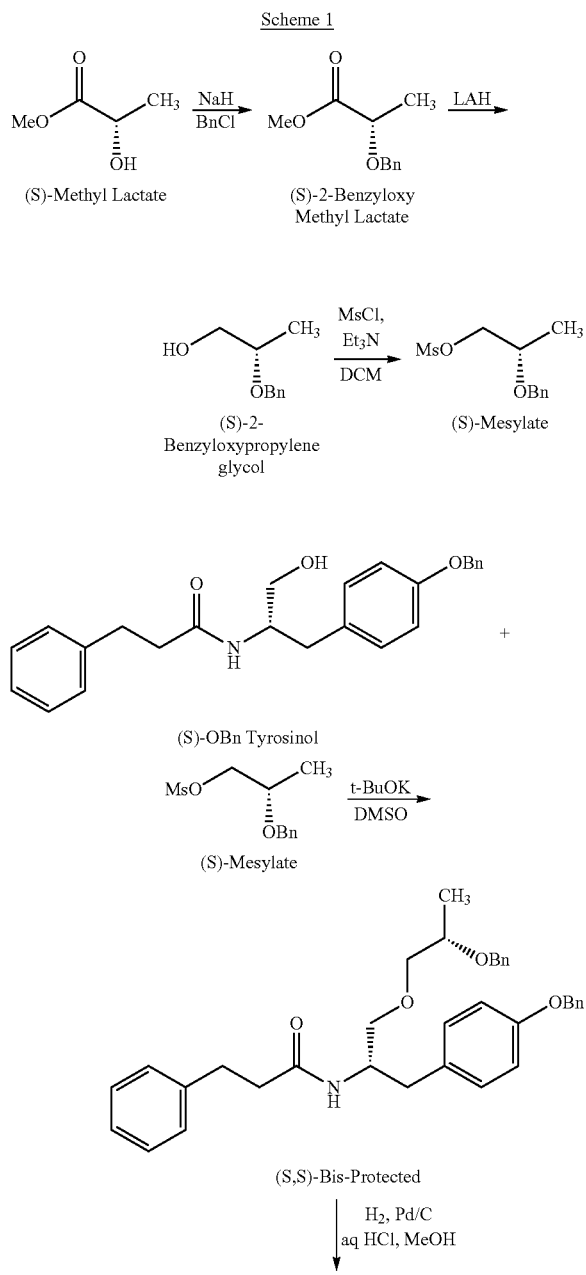

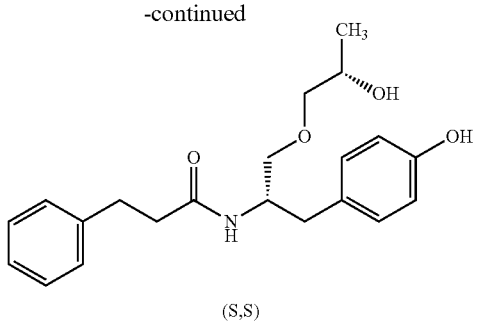

(S,S)

The (S,R) enantiomer may be synthesized accordingly, by reacting (S)—OBnTyrosinol with (R)-Mesylate to form (S,R)-Bis-Protected.

One of the problems that may be encountered in a synthesis procedure of chiral compounds is the occurrence of racemization in one (or more) of the synthetic steps. It is shown here, for the first time that the reaction temperature and the order of addition of the raw materials play a very important role in the chiral purity of the product formed. It was further shown that racemization occurs specifically at the first reaction step which involves the conversion of methyl lactate (S or R enantiomer) into 2-benzyloxy methyl lactate (S or R enantiomer). According to some embodiments, in order to reduce the occurrence of racemization in the process for the preparation of the (S,S) or (S,R) compounds, in the first reaction step, benzyl bromide and methyl lactate are to be mixed together prior to their addition to the base solution (e.g. sodium hydride). According to some embodiments the occurrence of racemization may be reduced upon performing the reaction at a temperature lower than room temperature, preferably, lower than 10° C., preferably, lower than 5° C., preferably, lower than 2° C., more preferably at a temperature lower than −10° C., most preferably at a temperature of −15° C. or lower. According to some certain preferred embodiments, the least racemization (i.e. <1%) racemization) was obtained by slurring sodium hydride in THF at a temperature of at least about −10° C., preferably of at least about −15° C. A mixture of (S) methyl lactate and benzyl bromide was added to the sodium hydride solution at a temperature of at least about −10° C., preferably of at least about −15° C.

It has been further found for the first time, that the yield of the reaction step which involves the reaction of (S)—OBn-Tyrosinol and Mesylate (S or R enantiomer) may be increased according to some embodiments, to about 15%, preferably to about 20%, more preferably to about 25% upon using DMF as the solvent instead of DMSO and sodium hydride as a base instead of potassium tert-butoxide. Each possibility represents a separate embodiment of the invention.

The present invention provides a therapeutic agent for treating or preventing pain, preferably neuropathic pain, comprising (S)2-N(3-O—((S)propan 2-ol)-1-propyl-4-hydroxybenzene)-3-phenylpropylamide as an active ingredient; a pharmaceutical composition for treating or preventing pain, preferably neuropathic pain, comprising a therapeutically effective amount of (S)2-N(3-O—((S)propan 2-ol)-1-propyl-4-hydroxybenzene)-3-phenylpropylamide and a pharmaceutically acceptable carrier and methods for treating or preventing pain, specifically neuropathic pain comprising the administration of a pharmaceutical composition comprising a therapeutically effective amount of S)2-N(3-O—((S)propan 2-ol)-1-propyl-4-hydroxybenzene)-3-phenylpropylamide.

Non limiting examples of neuropathic pain include neuropathic pains in post herpetic neuralgia, trigeminal neuralgia, diabetic neuralgia, cancer pain, persistent postoperative or posttraumatic pain, non-specific lower back pain, hyperalgia, allodynia, sciatica, postthoracotomy pain, CRPS, pain associated with multiple sclerosis, AIDS (or HIV-related neuropathy), fibromyalgia, thalamic pain, paraplegic pain caused by myelopathy, anesthesia dolorosa, phantom limb pain and the like. A therapeutic agent for neuropathic pain according to the present invention is especially effective for treating hyperalgia and allodynia. In addition, neuropathic pain conditions include pain associated with normally non-painful sensations such as "pins and needles" (paraesthesias and dysesthesias), increased sensitivity to touch (hyperesthesia), painful sensation following innocuous stimulation (dynamic, static, thermal or cold allodynia), increased sensitivity to noxious stimuli (thermal, cold, mechanical hyperalgesia), continuing pain sensation after removal of the stimulation (hyperpathia) or an absence of or deficit in selective sensory pathways (hypoalgesia).

The term "therapeutically effective amount" is that amount of the substantially pure (S)2-N(3-O—((S)propan 2-ol)-1-propyl-4-hydroxybenzene)-3-phenylpropylamide which is sufficient to provide a beneficial effect to the subject to which the substantially pure (S)2-N(3-O—((S)propan 2-ol)-1-propyl-4-hydroxybenzene)-3-phenylpropylamide is administered. More specifically, a therapeutically effective amount means an amount of the substantially pure (S)2-N(3-O—((S)propan 2-ol)-1-propyl-4-hydroxybenzene)-3-phenylpropylamide effective to alleviate or ameliorate the symptoms of pain in the subject being treated.

In the context of the present invention, the term "treatment" refers to symptomatic treatment and the term "prophylaxis" is used to mean preventing symptoms in an already afflicted subject or preventing recurrence of symptoms in an afflicted subject and is not limited to complete prevention of an affliction.

The therapeutic agent for the treatment or prevention of pain according to the present invention is selected from substantially pure (S)2-N(3-O—((S)propan 2-ol)-1-propyl-4-hydroxybenzene)-3-phenylpropylamide may be administered orally or parenterally with no specific limitation on the manner of administration. (S)2-N(3-O—((S)propan 2-ol)-1-propyl-4-hydroxybenzene)-3-phenylpropylamide as an active ingredient of the therapeutic agent for neuropathic pain according to the present invention may be provided independently, or provided as being contained in a formulation together with a pharmaceutically acceptable carrier or a pharmaceutical additive.

Examples of the pharmaceutically acceptable carrier or additive usable in the present invention include excipient, disintegrator, binder, lubricant, coating agent, colorant, diluent, dissolving agent, dissolution aid, tonicity agent, pH modifier, stabilizer, and the like.

Suitably, the composition of the present invention may be formulated as a unit dosage form. Each unit dosage form may comprise all or a predetermined fraction of the daily dose amount of the one or more compounds of the invention, e.g., one half or one quarter of the daily dose amount.

Thus, the composition may be formulated as a tablet, a pill, a capsule, a powder, fine granule, granules, a sterile parenteral solution or suspension, a metered aerosol or liquid spray, syrup, drops, an ampoule, an auto-injector device, a suppository, a cream or a gel. Said composition may be adapted for oral, enteral, parenteral, intrathecal, intranasal, sublingual, rectal or topical administration, or for administration by inhalation or insufflation. Oral compositions such as tablets, pills, capsules or wafers are particularly preferred.

For preparing a solid dosage form such as a tablet, said one or more compounds may be mixed with one or more pharmaceutical excipients, e.g., microcrystalline cellulose, sodium citrate, calcium carbonate, dipotassium phosphate, glycine and the like may be used together with any of various disintegrators such as starch (preferably corn, potato or tapioca starch), alginic acid, a certain type of silicate double salt and the like; and a granule-forming binder such as polyvinylpyrrolidone, sucrose, gelatin, gum arabic or the like. A lubricant such as magnesium stearate, sodium lauryl sulfate, talc or the like is often very effective for tablet formation. A gelatin capsule filled with the same type of solid composition may be used. Substances preferably usable in connection with this include lactose as well as high-molecular-weight polyethylene glycol. For preparing an aqueous suspension and/or elixir for oral administration, the active ingredient may be used together with any of various types of sweeteners, flavorings, coloring agents or dyes, optionally an emulsifier and/or a suspending agent, as well as a diluent such as water, ethanol, propylene glycerol, glycerol, or the like or a combination thereof.

According to some embodiments, the solid pre-formulation composition is then subdivided into unit dosage forms of the kind mentioned above which each may contain from 0.1 mg to about 500 mg of the compounds of the invention. According to some embodiments, the unit dosage forms contain from 1 mg to 500 mg, e.g. 1, 5, 10, 25, 50, 100, 200, 300 or 500 mg of the compounds.

According to some embodiments, when formulated as a tablet or pill, said tablet or pill may be coated or otherwise compounded to provide a dosage form affording the advantage of prolonged action. For instance, said tablet or pill can comprise an inner dosage and an outer dosage component, the latter being in the form of an envelope over the former. These two components may be separated by an enteric layer that serves to resist disintegration in the stomach and permits the inner component to pass intact into the duodenum or to be delayed in release. A variety of materials are known in the use in such enteric layers or coatings, such materials including a number of polymeric acids and mixtures of polymeric acids with such materials as shellac, cetyl alcohol and cellulose acetate.

According to some embodiments the pharmaceutical composition of the present invention may be formulated as a liquid dosage form for administration orally or parentally by injection suppository and the like; for example an aqueous solution, a suitably flavored syrup, an aqueous or oil suspension or a flavored emulsion with edible oils such, for example, as cottonseed oil, sesame oil, coconut oil or peanut oil, as well as an elixir or a similar pharmaceutical vehicle. Suitable dispersing or suspending agents for an aqueous suspension include synthetic and natural gums, e.g., tragacanth, acacia, alginate, dextran, sodium carboxymethylcellulose, methylcellulose, polyvinyl-pyrrolidone or gelatin. When necessary, the aqueous solution is appropriately buffered (preferably to pH 8 or higher) to first isotonize the liquid diluent. Such an aqueous solution is suitable for intravenous injection, and an oleaginous solution is suitable for intraarticular injection, intramuscular injection and subcutaneous injection. The liquid dosage form can be easily produced under aseptic conditions by a standard pharmaceutical technology well known to those skilled in the art. In addition, the active ingredient of the present invention may be topically administered to skin or the like. In such a case, it is desirable to topically administer the active ingredient in the form of cream, jelly, paste or ointment in accordance with the standard pharmaceutical practice.

A therapeutic agent for neuropathic pain according to the present invention may be administered in an appropriate dose, with no specific limitation, which is selected in accordance with various conditions including the type of pain, age or symptom of the patient, administration route, purpose of treatment, and presence or absence of another medication used together with the agent. A daily dose of the therapeutic agent for neuropathic pain according to the present invention is, for example, about 0.1 mg/Kg body weight to about 100 mg/Kg body weight, preferably 1 to 50 mg/Kg body weight, more preferably 5-30 mg/Kg body weight.

EXAMPLES

The following examples are intended to illustrate the disclosure and without however limiting the scope thereof.

Example 1

The Synthesis of E1

The general synthesis procedure of E1 is summarized in Scheme 1. Specifically, E1 was synthesized using the process comprising the following steps:
1. 2 gr of methyl lactate was reacted with excess of benzyl bromide to get 880 mg of (S)-benzyloxymethyl lactate. The reaction was performed by slurring sodium hydride in THF and cooling down to approximately −15° C. The reaction mixture was then allowed to warm slowly to room temperature and stirred for approximately 1 to 2 hours. The reaction was quenched with saturated ammonium chloride solution and extracted with MTBE twice followed by the removal of solvent on a rotary evaporator to get a crude oil. The crude product was purified by column chromatography to get pure (S)-2-benzyloxymethyl lactate. (R)-2-benzyloxymethyl lactate isomer was present at 0.93% only. According to some embodiments, the yield of this step may be increased by avoiding the presence of moisture in the reaction solution (i.e. THF).
2. 880 mg (S)-2-benzyloxymethyl lactate obtained in step 1 were reduced using lithium aluminum hydride to get (S)-2-benzyloxypropylene glycol in 83.8% yield with 98.7% purity. A solution of pure (S)-2-benzyloxymethyl lactate in methylene chloride was stirred and a solution of lithium aluminum hydride was slowly added to it at approximately 5° C. The reaction was monitored by the TLC system and quenched by USP-PW water very carefully. No racemization occurred in this step.
3. (S)-2-benzyloxypropylene glycol was then reacted with methane sulfonyl chloride in methylene chloride in the presence of triethyl amine to get the mesylate in 88% yield. A solution of step 2 was stirred in methylene chloride and methane sulfonyl chloride was added to it dropwise at <5° C. After the addition was completed, the progress of the reaction was monitored by the TLC system. The reaction was quenched with USP-PW water. After the layers were separated, the aqueous layer was back extracted with methylene chloride. The methylene chloride layers were then combined and washed with USP-PW water 3 times to remove most of the methane sulfonic acid. No racemization occurred in this step.
4. The mesylate (of step 3) was coupled with S-Obenzyl tyrosinol to form bis protected E1 in 22.7% yield, with purity of 97.4%. The reaction was carried out at room temperature using a combination of DMF as the solvent and sodium hydride as the base. The reaction went to completion after stirring for at least 12 hours at room temperature.

When DMSO was used as a solvent with potassium tert-butoxide as a base, it appeared that the demsyl anion form by the reaction of the base with DMSO decomposes the mesylate or converts it into impurities. As a result either only traces of the product or no product was formed.
5. 340 mg of the product of step 4 was reduced by hydrogenation in the presence of 10% palladium on carbon catalyst and hydrochloric acid using methylene chloride as a solvent at 50° C. The reaction went to completion in approximately 4 hours with no racemization to yield E1 in 84.3% yield and 98.9%.

Example 2

The Synthesis of E2

The E2 enantiomer was synthesized as the racemate of the (S,S) and the (S,R) enantiomers as described in US 2011/0086910 and was further separated on RegisPack™ column, a polysaccharide coated chiral column (with a tris-(3,5-dimethylphenyl) carbamoyl cellulose selector) (FIG. 7A-C).

Example 3

Evaluation of the Analgesic Effect of E1 and E2 in a Tail Flick Test

In the present study the analgesic effect of the substantially pure enantiomers E1 and E2 was evaluated using the tail flick model for nociceptive pain in mice.
Preparation of the Test Items and Materials:

| Group | Compound | Group size | Dose (mg/kg) | Route | Dosing Volume |
|---|---|---|---|---|---|
| 1 | Vehicle | 3 | 0 | IP | 5 ml/kg |
| 2 | Morphine | 3 | 5 | | |
| 3 | E1 | 6 | 3 | | |
| 4 | E1 | 6 | 10 | | |
| 5 | E1 | 6 | 20 | | |
| 6 | E2 | 6 | 10 | | |

Morphine Preparation: 19 ml saline was added to 1 ml morphine ampoule and 0.1 ml of received solution was injected per 20 g mice (5 ml/kg).
Vehicle Preparation: 1 ml DMSO was dissolved in 4 ml saline.
E1 and E2 sample Preparation (concentration of 2 mg/ml for dosing of 10 mg/kg):
  4 mg of E1 or E2 was weighed.
  The measured E1 or E2 was completely dissolved in 0.4 ml DMSO.
  The solution was then diluted in 1.6 ml saline.
Preparation of E1 for Part B:
E1 Stock Solution was Prepared as Follows:
  16.5 mg of E1 was weighed.
  The measured E1 was completely dissolved in 0.82 ml DMSO.
  The solution was then diluted in 3.28 ml saline.

E1 Preparation (Concentration of 4 mg/ml for Dosing of 20 mg/kg):

20 mg/kg of E1 solution was dosed from stock solution via IP administration in a 5 ml/kg injection volume.

E1 Preparation (Concentration of 2 mg/ml for Dosing of 10 mg/kg):

0.7 ml from stock solution was diluted in 0.7 ml Vehicle.

10 mg/kg of E1 solution was dosed from stock solution via IP administration in a 5 ml/kg injection volume.

E1 Preparation (Concentration of 0.6 mg/ml for Dosing of 3 mg/kg):

0.5 ml from stock solution was diluted in 3.35 ml Vehicle.

3 mg/kg of E1 solution was dosed from stock solution via IP administration in a 5 ml/kg injection volume The Test System (See Table 1):

The experiment was performed using male ICR strain 7 weeks old mice (25-27 g) (supplied by Harlan Israel, Ltd.)

The experiment included a total number of 18 mice (part A) and 20 mice (part B).

The weight variation of animals at the time of treatment initiation did not exceed ±20% of the mean weight.

The health status of the animals used in this study was examined upon their arrival. Only animals in good health were acclimatized to laboratory conditions and were used in the study.

Animals were acclimated for 5 days. During acclimation and throughout the entire study duration, animals housed within a limited access rodent facility and kept in groups with a maximum of 6 mice per polypropylene cages. The cages were fitted with solid bottoms and filled with sterile wood shavings as bedding material. Animals were provided ad libitum with a commercial, sterile rodent diet and had free access to drinking water that was supplied to each cage via polyethylene bottles with stainless steel sipper tubes. Water was monitored periodically. Automatically controlled environmental conditions were set to maintain temperature at 20-24° C. with a relative humidity (RH) of 30-70%, a 12:12 hour light:dark cycle and 15-30 air changes/h in the study room. Temperature and RH were monitored daily.

During experiment each dosing group was kept in separate cages to avoid cross-contamination which can occur through consumption of fecal matter. At the end of the study, surviving animals were euthanized by $CO_2$ asphyxiation.

TABLE 1

Test groups and dose regimen of the present study:

| Group No. | Compound | Group size | Dose (mg/kg) | Route | Dosing Volume | Time o administration |
|---|---|---|---|---|---|---|
| 1 | Vehicle | 3 | 0 | IP | 5 ml/kg | Test items were administered 0.5 hour prior to tail flick testing |
| 2 | Morphine | 3 | 5 | | | |
| 3 | E1 | 6 | 3 | | | |
| 4 | E1 | 8 | 10 | | | |
| 5 | E1 | 6 | 20 | | | |
| 6 | E2 | 6 | 10 | | | |

Principles of the Tail Flick Test:

Response to pain was assessed using the tail flick method which utilizes an Ugo Basile tail flick instrument. The animal is placed and held gently on the Ugo Basile tail flick (TF) instrument surface with the tail straight back and above a photoelectric cell that served as heat source. The heat source and timer are turned on by a foot pedal press, and automatically switch off when the animal flicks its tail off the emitter. Latency is measured and analyzed as an analgesic effect.

Description of the Study: The baseline tail flick was measured a day before the experiment started. On the day of the experiment, animal body weights were first measured followed by the IP administration of the test items (vehicle, morphine, NRD 13 S E1 and E2). 30 minutes after administration of the test items, the animals were subjected to the tail-flick testing. The tail-flick experiments were followed by blood sampling of all groups. The experiment was terminated after spinal cords and brains of all groups have been collected.

Statistics and Data Evaluation: All parameters are represented as means and standard error of the mean (SEM). Data was analyzed using a two tailed, unpaired T-test to compare each treatment group to the Vehicle treated animals. A two-tailed, paired T-test was used to compare the pre-treatment and post-treatment of each treatment group. Probability values $p<0.01$ and $p<0.05$ are considered significant.

Results:

Body Weight: The mean body weight for all the animals was 27.42±0.22 g. No statistical differences were found between groups.

Figure 1:
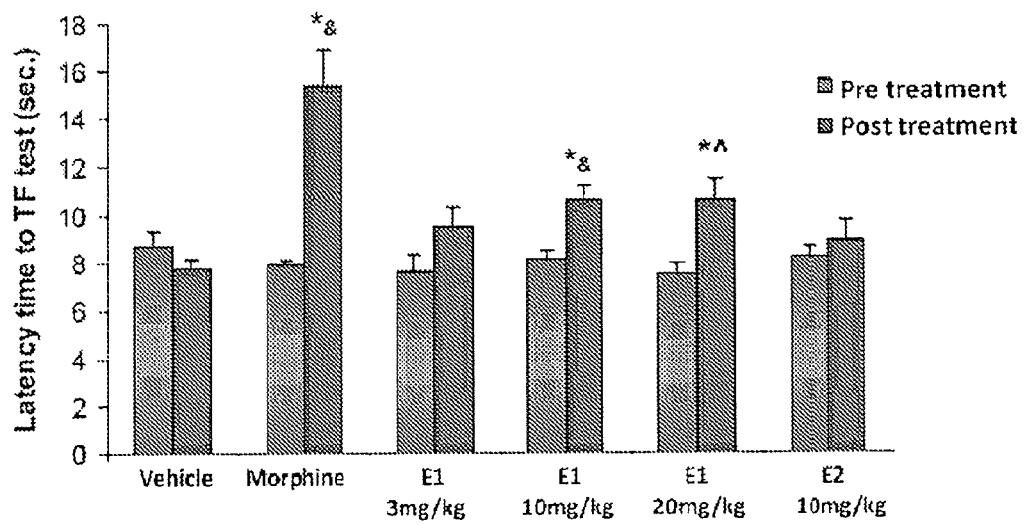
FIG. 1 shows the mean latency time measures using the tail flick test. Study groups from left to right include: vehicle (group 1); Morphine (group 2); 3 mg/kg of substantially pure (S)2-N(3-O—((S)propan 2-ol)-1-propyl-4-hydroxybenzene)-3-phenylpropylamide (group 3); 10 mg/kg of substantially pure (S)2-N(3-O—((S)propan 2-ol)-1-propyl-4-hydroxybenzene)-3-phenylpropylamide (group 4); 20 mg/kg of substantially pure (S)2-N(3-O—((S)propan 2-ol)-1-propyl-4-hydroxybenzene)-3-phenylpropylamide (group 5) and 10 mg/kg of substantially pure (S)2-N(3-O—((R)propan 2-ol)-1-propyl-4-hydroxybenzene)-3-phenylpropylamide (group 6). *=$p<0.01$ vs. Vehicle; &=$p<0.05$ Pretreatment vs. Post-treatment; ^=$p<0.05$ Pretreatment vs. Post-treatment.
Figure 2:
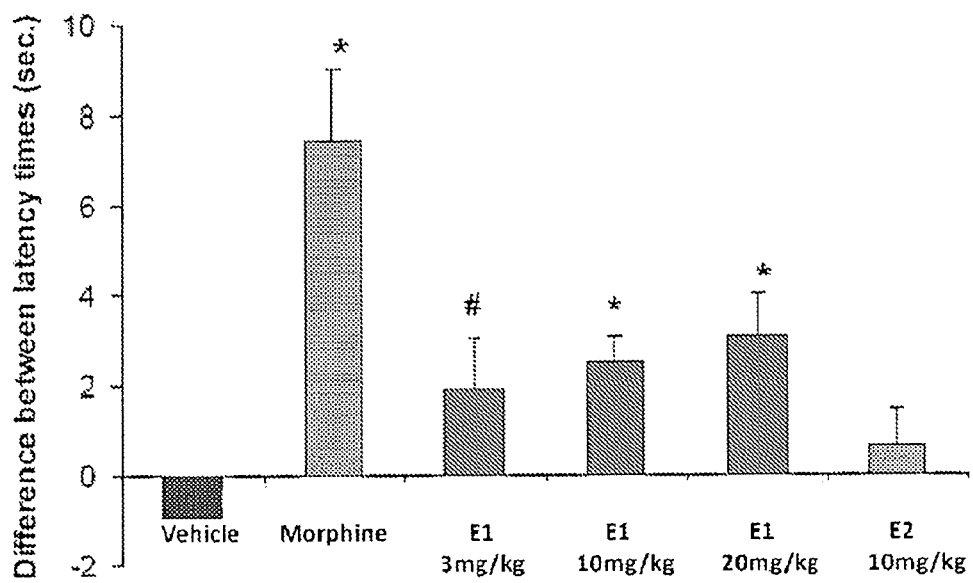
FIG. 2 shows the difference between post-treatment and pre-treatment latency times measured using the tail flick (sec). Study groups from left to right include: vehicle (group 1); Morphine (group 2); 3 mg/kg of substantially pure (S)2-N(3-O—((S)propan 2-ol)-1-propyl-4-hydroxybenzene)-3-phenylpropylamide (group 3); 10 mg/kg of substantially pure (S)2-N(3-O—((S)propan 2-ol)-1-propyl-4-hydroxybenzene)-3-phenylpropylamide (group 4); 20 mg/kg of substantially pure (S)2-N(3-O—((S)propan 2-ol)-1-propyl-4-hydroxybenzene)-3-phenylpropylamide (group 5) and 10 mg/kg of substantially pure (S)2-N(3-O—((R)propan 2-ol)-1-propyl-4-hydroxybenzene)-3-phenylpropylamide (group 6). *=$p<0.01$ vs. Vehicle; #=$p<0.05$ vs. Vehicle.

Tail Flick Test:

The results of the tail flick test are presented in FIG. 1 as the latency time (seconds) it takes for the animal to flick their tail away from the heat source. Results are also presented as the difference between post-treatment TF latency times minus the TF latency time of pre-treatment (FIG. 2). An increase in difference between latency times presents a more healthy state for the animals.

The Latency Time to Tail Flick (sec) are summarized in Table 2, columns 4-5: The mean latency time for the Vehicle treated animals (Group 1) at baseline (pre-treatment) was 8.72±0.65 sec. Thirty minutes post drug administration the mean latency time was 7.78±0.36 sec, which is not statistically different from baseline.

Treatment with morphine (Group 2) at a dose of 5 mg/kg was significantly effective in increasing the latency time when compared to the pre-treatment value: 7.92±0.17 sec pretreatment vs. 15.38±1.47 sec post-treatment ($p<0.01$).

Treatment with E1 at a dose of 10 mg/kg (Group 4) was significantly effective in increasing the latency time when compared to the pre-treatment value: 8.16±0.39 sec pretreatment vs. 10.63±0.64 sec post-treatment ($p<0.01$). In addition, treatment with E1 at a dose of 10 mg/kg and 20 mg/kg expressed pain relief activity when compared to the Vehicle treated animals (Group 1): 10.63±0.64 sec (Group 4) and 10.65±0.81 sec (Group 5) vs. 7.78±0.36 sec Vehicle ($p<0.01$).

Although latency times increased between the pretreatment and post treatment states, this increase was not statistically significant for treatment with E1 at a dose of 3 mg/kg or with E2 at a dose of 10 mg/kg. Additionally, these treatments were not significantly active in reducing pain when compared to the Vehicle.

Difference Between Tail Flick Latency Times for Pre-Treatment and Post-Treatment (sec):

The greater the difference between pretreatment and post treatment latency times, the greater the pain relief activity. This difference is summarized in Table 2, right column. It can be seen that E1 showed significant pain relief activity when compared to the Vehicle treated, in particular at doses of 10 and 20 mg/kg ($p<0.01$). In contrast, E2 did not cause any statistically significant difference in tail flick latency times.

TABLE 2

Tail Flick experiment data summary

| Group No. | Compound | Average body weight | Mean latency time (sec) Pre-treatment | Mean latency time (sec) Post-treatment | Δ of latency time post- and pre-treatment (sec) |
|---|---|---|---|---|---|
| 1 | Vehicle | 27.70 ± 0.49 | 8.72 ± 0.65 | 7.78 ± 0.36 | −0.93 ± 0.50 |
| 2 | Morphine | 27.43 ± 0.70 | 7.92 ± 0.17 | 15.38*& ± 1.47 | 7.47* ± 1.53 |
| 3 | E1 | 26.83 ± 0.48 | 7.62 ± 0.74 | 9.53 ± 0.85 | 1.92# ± 1.10 |
| 4 | E1 | 27.44 ± 0.38 | 8.16 ± 0.39 | 10.63*& ± 0.64 | 2.46* ± 0.60 |
| 5 | E1 | 28.00 ± 0.45 | 7.58 ± 0.41 | 10.65*^ ± 0.81 | 3.07* ± 0.92 |
| 6 | E2 | 27.13 ± 0.76 | 8.30 ± 0.46 | 8.93 ± 0.93 | 0.63 ± 0.87 |

\* = $p < 0.01$ vs. Vehicle
& = $p < 0.05$ Pretreatment as measured for group No. 4 vs. Post-treatment
^ = $p < 0.05$ Pretreatment as measured for group No. 5 vs. Post-treatment
# = $p < 0.05$ vs. Vehicle Conclusions:

In view of the findings obtained under the conditions of this study and confined to the in-life data, E1 at doses of 10 mg/kg and 20 mg/kg was active in reducing pain when compared to the Vehicle treated group in tail flick model for nociception.

Test Item E1 at a dose of 3 mg/kg showed significant pain relief activity only in the calculated difference between TF latency times for pre-treatment and post-treatment, suggesting the trend of activity. E2 at a dose of 10 mg/kg was not active in this study.

Example 4

Evaluation of the Therapeutic Activity of E1 Using the Spinal Nerve Ligation (Chung) Model in Rats The antinociceptive and analgesic activity of E1 in a spinal nerve ligation (SNL or Chung) model for neuropathic pain in rats was evaluated.

On study day 0, all animals underwent Chung surgery, which consisted of an operation where the left L5-L6 spinal nerves were isolated and cut. Fourteen days post surgery the animals were selected using pain threshold results from the Von Frey test. Only animals that indicated signs of mechanical allodynia were included in the study. After the selection process, the animals were grouped and Test Items were administered via IP. The pain response was measured using Von Frey methodology at 2, 5 and 24 hours after Test Item administration on study day 14, and at 2, 5, 24 and 48 hours on study day 21 after 7 days of Test Item administration.

All animals gained weight during the study. There were no significant differences in body weight gain between the groups. This increase in body weight reflects general good health throughout the study.

Materials and their Preparation:

Vehicle: 1 ml DMSO (Sigma) was dissolved in 4 ml saline (Supplier: TEVA medical).

Positive Control: Gabapentin (supplier: USP) exists as a powder. To achieve a dose of 150 mg/kg, 250 mg of gabapentin was dissolved in 5 ml saline (50 mg/ml).

A rat weighing 200 g was injected with 0.6 ml of dissolved solution.

E1 Stock Solution: 2.43 g of E1 was dissolved completely in 81 ml DMSO.

E1 Preparation (concentration of 6 mg/ml for dosing of 30 mg/kg): 3 ml from stock was diluted with 12 ml saline.

E1 Preparation (concentration of 3 mg/ml for dosing of 15 mg/kg): 1.5 ml from stock was diluted with 1.5 ml DMSO and 12 ml saline.

E1 Preparation (concentration of 1.5 mg/ml for dosing of 7.5 mg/kg): 0.75 ml from stock was diluted with 2.25 ml DMSO and 12 ml saline.

For all formulations the application volume was 5 ml/kg.

Test System:

The test groups and dose regimen of the present study are summarized in Table 3.

Species: 50 SD young adult male rats, 225-260 g at study initiation (Harlan Laboratories, Israel. Ltd.)

Body Weight: Weight variation of animals at the time of treatment initiation did not exceed ±20% of the mean weight.

Animal Health: The health status of the animals used in this study was examined upon their arrival. Only animals in good health were acclimatized to laboratory conditions and were used in the study.

Acclimation: 5 days.

Housing: During acclimation and throughout the entire study duration, animals were housed within a limited access rodent facility and kept in groups with a maximum of 3 rats per polypropylene cages. The cages were fitted with solid bottoms and filled with sterile wood shavings as bedding material.

Food and Water: Animals were provided ad libitum with a commercial, sterile rodent diet and had free access to drinking water that was supplied to each cage via polyethylene bottles with stainless steel sipper tubes. A feed lot analysis of the diet batch used in the study was included in the archives with the study data. Water was monitored periodically.

Environment: Automatically controlled environmental conditions were set to maintain temperature at 20-24° C. with a relative humidity (RH) of 30-70%, a 12:12 hour light:dark cycle and 15-30 air changes/h in the study room. Temperature and RH were monitored daily. The light cycle was monitored by the control clock.

Each dosing group was kept in separate cages to avoid cross-contamination which could occur through consumption of fecal matter. 2 or 3 animals were housed per cage.

Termination: At the end of the study, surviving animals were euthanized by $CO_2$.

TABLE 3 test groups and dose regimen of the present study:

| Group # | Test Items | Volume | Dosing regime | Testing regime |
|---|---|---|---|---|
| 1 | Vehicle (DMSO) | 5 ml/kg | Once daily starting on study day 14 through study day 21. On study day 14 2, 5 and 24 hours prior to Von Frey testing. On study day 21 2, 5, 24 and 48 hours prior to Von Frey testing. | Von Frey testing at 2, 5 and 24 hours after dosing on study day 14 and at 2, 5, 24 and 48 hours after dosing on study day 21. On study day 15 Von Frey testing prior to test Item's administration |
| 2 | Gabapentin 150 mg/kg IP | 5 ml/kg | On study day 14 2, 5 and 24 hours prior to Von Frey testing. On study day 21 2, 5, 24 and 48 hours prior to Von Frey testing. | Von Frey testing at 2, 5 and 24 hours after dosing on study day 14 and at 2, 5, 24 and 48 hours after dosing on study day 21. |
| 3 | E1 30 mg/kg IP | 5 ml/kg | Once daily starting on study day 14 through study day 21. On study day 14 2, 5 and 24 hours prior to Von Frey testing. On study day 21 2, 5, 24 and 48 hours prior to Von Frey testing. | Von Frey testing at 2, 5 and 24 hours after dosing on study day 14 and at 2, 5, 24 and 48 hours after dosing on study day 21. On study day 15 Von Frey testing prior to test Item's administration |
| 4 | E1 15 mg/kg IP | 5 ml/kg | Once daily starting on study day 14 through study day 21. On study day 14 2, 5 and 24 hours prior to Von Frey testing. On study day 21 2, 5, 24 and 48 hours prior to Von Frey testing. | Von Frey testing at 2, 5 and 24 hours after dosing on study day 14 and at 2, 5, 24 and 48 hours after dosing on study day 21. On study day 15 Von Frey testing prior to test Item's administration |
| 5 | E1 7.5 mg/kg IP | 5 ml/kg | Once daily starting on study day 14 through study day 21. On study day 14 2, 5 and 24 hours prior to Von Frey testing. On study day 21 2, 5, 24 and 48 hours prior to Von Frey testing. | Von Frey testing at 2, 5 and 24 hours after dosing on study day 14 and at 2, 5, 24 and 48 hours after dosing on study day 21. On study day 15 Von Frey testing prior to test Item's administration |

Test Procedure:

Principles of the Chung Induced Model: The Chung model is a reliable model for neuropathy pain that enables the measurement of the animal's pain threshold immediately after the animal awakes from surgery.

The Study schedule (study day 1 through study day 14) including operation and treatment is summarized in table 4:

TABLE 4

Therapeutic activity of E1 using the spinal nerve ligation (Chung) model in rats. Study schedule:

| Day | Task |
|---|---|
| −1 | Von Frey response measurements (baseline); Body weight measurements. |
| 0 | Chung operation. |
| 7 | Body weight measurements. |
| 14 | 1. Von Frey response measurements (pre-TI administration); 2. Selection and grouping; 3. Body weight measurements; 4. Test Items' administration to all groups; 5. Von Frey response measurements (2 and 5 hours post-TI administration). |
| 15 | Von Frey response measurements (24 hours post-TI administration); Test Items' administration to all groups. |

TABLE 4-continued

Therapeutic activity of E1 using the spinal nerve ligation (Chung) model in rats. Study schedule:

| Day | Task |
|---|---|
| 16-20 | Vehicle (Group 1M) and E1 (Groups 3M-5M) administration. |
| 21 | 1. Von Frey response measurements (pre-TI administration); 2. Body weight measurements; 3. Test Items administration to all groups; 4. Von Frey response measurements (2 and 5 hours post-TI administration). |
| 22 | 1. Von Frey response measurements (24 hours post-TI administration). |
| 23 | 1. Von Frey response measurements (48 hours post-TI administration); 2. Termination |

Neuropathic Pain Induction: While under anesthesia using ketamine/xylazine sodium and after the area was shaved, the rat was placed in a prone position and the left paraspinal muscles were separated from the spinous process at the L4-S2 levels. The L6 vertebral transverse process was carefully removed with a small rongeur to visually identify the L5-L6 spinal nerves. The left L5-L6 spinal nerves were cut. The muscle was then closed with 4-0 silk sutures and the skin was closed by a clamp. Following surgery, the rats were returned to the cage and remained under a heating lamp until they awoke.

Inclusion/Exclusion Criteria for Pre-Selection: On post-operative day 14, animals were tested for mechanical allodynia using Von Frey methodology prior to being placed in their experimental groups. Only animals with a pain threshold of ≤26 g for the operated leg were included in the study. In order to form homogenous treatment groups and to adhere to randomization, all the operated rats were grouped according to inclusion/exclusion criteria.

Treatment:

Treatment Commencement: Animals were selected using the parameter of pain development (Von Frey testing) and then placed into their experimental groups.

Vehicle and E1 was administered from study day 14 through study day 21.

Gabapentin, the positive control, was administered only on the testing days 14, 15 and 21.

The Von Frey test was performed prior to Test Items' administrations (pre-TI injection) and at 2 and 5 hours after TI administration (post-TI injection) on study days 14 and 21.

Von Frey test was performed prior to TI's administration on study day 15 (24 hours post-TI's administration on study day 14) and on study days 22 and 23 (24 and 48 hours respectively post-TI's administration on study day 21).

Route of Administration: E1 (test item); vehicle and positive control (Gabapentin) were administered IP. In all instances, unless decided otherwise in the course of the study, all dosing solutions were applied as once a day administration on each of the repeated dosing sessions.

Termination: At the end of the study, the animals were euthanized with $CO_2$.

Experimental Observations:

Body Weights: Body weight was measured at regular intervals on study days −1 for baseline values and seven days after the surgery (study day 7). In addition, animals that demonstrated criterion for mechanical allodynia on study day 14 were also weighed after selection and grouping on study days 14 and 21.

Pain Response Evaluation: Pain response was evaluated using Von Frey test for mechanical allodynia.

The Von Frey test for mechanical allodynia is based on applying short pulses of pressure that are not painful to a naive animal. In fact, in order to achieve paw withdrawal from a naive animal, the pressure applied is sometimes higher than 60 g. This often requires the researcher to apply enough pressure with the Von Frey filament to actually lift the paw of the naive animal. However, in disease conditions, the animals are sensitive to much lower pressure and experience pain as a result of a normally non-painful stimulus.

Mechanical Allodynia Evaluation (Von Frey Testing): Allodynic response to tactile stimulation was assessed using the Von Frey apparatus (Touch®).

The rats were placed in an enclosure and positioned on a metal mesh surface, but allowed to move freely. The rats' cabins were covered with red cellophane to diminish environmental disturbances. The test began after cessation of exploratory behavior. The set of Von Frey monofilaments provide an approximate logarithmic scale of actual force and a linear scale of perceived intensity as provided by the manufacturer of the Von Frey apparatus (Ugo Basil). The operating principle: When the tip of a fiber of given length and diameter is pressed against the skin at right angles, the force of application increases as long as the researcher continues to advance the probe until the fiber bends. After the fiber bends, the probe continues to advance, causing the fiber to bend more, but without additional force being applied to the paw.

TABLE 5 the force (g) and its corresponding size of monofilaments

| size | Force (g) |
|---|---|
| 1.65 | 0.008 |
| 2.36 | 0.02 |
| 2.44 | 0.04 |
| 2.83 | 0.07 |
| 3.22 | 0.16 |
| 3.61 | 0.40 |
| 3.84 | 0.60 |
| 4.08 | 1.00 |
| 4.17 | 1.40 |
| 4.31 | 2.00 |
| 4.56 | 4.00 |
| 4.74 | 6.00 |
| 4.93 | 8.00 |
| 5.07 | 10 |
| 5.18 | 15 |
| 5.46 | 26 |
| 5.88 | 60 |
| 6.10 | 100 |
| 6.45 | 180 |
| 6.65 | 300 |

Rodents exhibit a paw withdrawal reflex when its paw is unexpectedly touched. The Touch Test™ Sensory Evaluator can be used on the plantar surfaces of the rat's foot. The animal will indicate sensation by pulling back its paw. The minimal force needed to elevate the withdrawal reflex is designated/considered as the value of reference.

Statistics/Data Evaluation: All data are presented as means±SEM. Each treatment group was compared to its relevant Vehicle group using a two-tailed, unpaired T-test (Software: Microsoft®Excel). A two-tailed, paired T-test was used to compare pre-treatment pain response to post-treatment pain response for each test group. A p value<0.05 is considered to represent a significant difference.

Von Frey test was performed on study days 22 and 23 (24 and 48 hours respectively post-TI's administration on study day 21).

Figure 3:
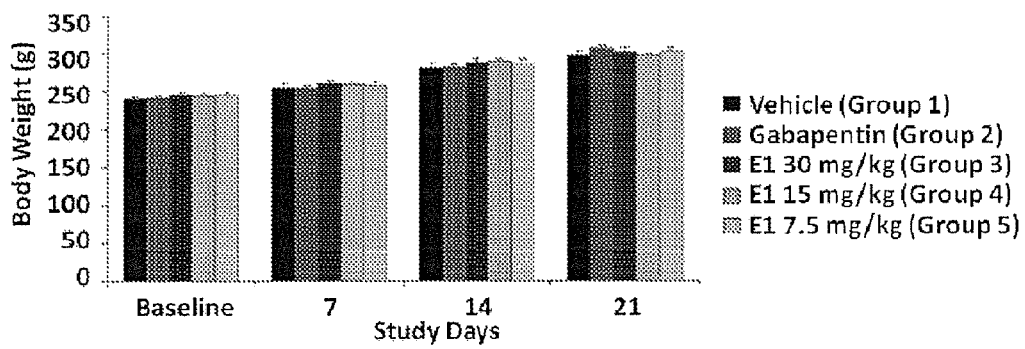
FIG. 3 shows the mean group body weight of the different study groups measured during the course of the study (day 1, 7, 14 and 21). Study groups from left to right include: vehicle (group 1); Gabapentin (group 2); 30 mg/kg of substantially pure (S)2-N(3-O—((S)propan 2-ol)-1-propyl-4-hydroxybenzene)-3-phenylpropylamide (group 3); 15 mg/kg of substantially pure (S)2-N(3-O—((S)propan 2-ol)-1-propyl-4-hydroxybenzene)-3-phenylpropylamide (group 4); 7.5 mg/kg of substantially pure (S)2-N(3-O—((S)propan 2-ol)-1-propyl-4-hydroxybenzene)-3-phenylpropylamide (group 5).

Results:

Body Weight (Table 6; FIG. 3): All animals gained weight during the study; however, there were no significant differences in weight gain between the groups. Baseline body weight for all animals was 243.76±1.21 g on study day −1.

Body weights were also measured on study days 7, 14 and 21. At study day 7, the mean body weight for all groups was 258.12±1.71 g. At study day 14, the mean body weight for all groups was 286.34±1.93 g. At study day 21, the mean body weight was 302.34±2.29 g.

the Vehicle treated animals (Group 1) was 56.60±3.40 g. On study day 14 prior to treatment, the withdrawal force of the left leg was significantly lower than the baseline measurement indicating a painful state: 10.00±0.93 g; $p<0.05$.

E1 30 mg/kg IP (Group 3): When compared to the Vehicle control (Group 1) treatment with E1 at a dose of 30 mg/kg on study day 14 did not inhibit allodynia 2 hours after its administration (13.20±1.70 g ns. vs. 10.70±0.98 g in the Vehicle group). Treatment with E1 at a dose of 30 mg/kg on study day 14 effectively inhibited allodynia at 5 hours after its admin-

TABLE 6

Mean group body weight in all study groups

| Group code | Treatment | Baseline | Day 7 | Day 14 | Day 21 |
|---|---|---|---|---|---|
| 1 | Vehicle DMSO | 240.70 ± 2.73 | 256.10 ± 4.32 | 282.30 ± 4.73 | 298.20 ± 6.12 |
| 2 | Gabapentin 150 mg/kg IP | 242.10 ± 2.44 | 255.20 ± 2.83 | 283.30 ± 2.53 | 307.90 ± 3.42 |
| 3 | E1 30 mg/kg IP | 245.20 ± 3.19 | 261.20 ± 4.45 | 288.70 ± 5.51 | 303.30 ± 6.01 |
| 4 | E1 15 mg/kg IP | 245.00 ± 2.80 | 259.20 ± 3.29 | 289.80 ± 3.27 | 298.50 ± 3.27 |
| 5 | E1 7.5 mg/kg IP | 245.80 ± 2.54 | 258.90 ± 4.41 | 287.60 ± 5.14 | 303.80 ± 6.26 |

Figure 4A:
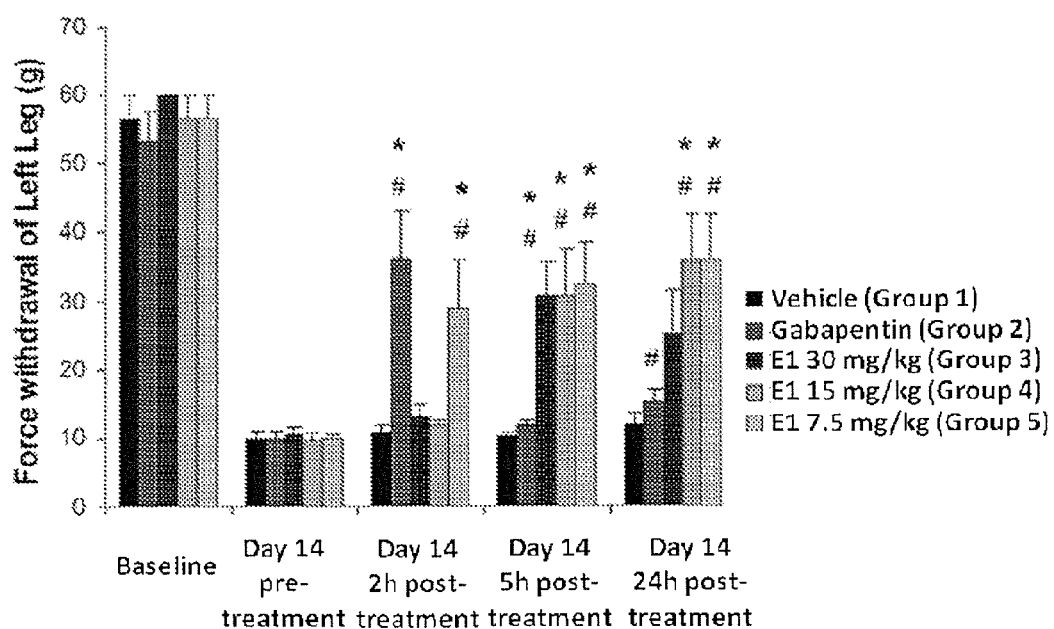
FIGS. 4A-4B show the mean Von Frey force required for withdrawal of left operated leg measured on the $14^{th}$ day of the study 2, 5 and 24 hours post treatment and on the $21^{st}$ day of the study 2, 5, 24 and 48 hours post 7 days treatment. Study groups from left to right include: vehicle (group 1); Gabapentin (group 2); 30 mg/kg of substantially pure (S)2-N(3-O—((S)propan 2-ol)-1-propyl-4-hydroxybenzene)-3-phenylpropylamide (group 3); 15 mg/kg of substantially pure (S)2-N(3-O—((S)propan 2-ol)-1-propyl-4-hydroxybenzene)-3-phenylpropylamide (group 4); 7.5 mg/kg of substantially pure (S)2-N(3-O—((S)propan 2-ol)-1-propyl-4-hydroxybenzene)-3-phenylpropylamide (group 5). * $p<0.05$ vs. Vehicle #$p<0.05$ Pretreatment vs. Post-treatment.
Figure 4B:
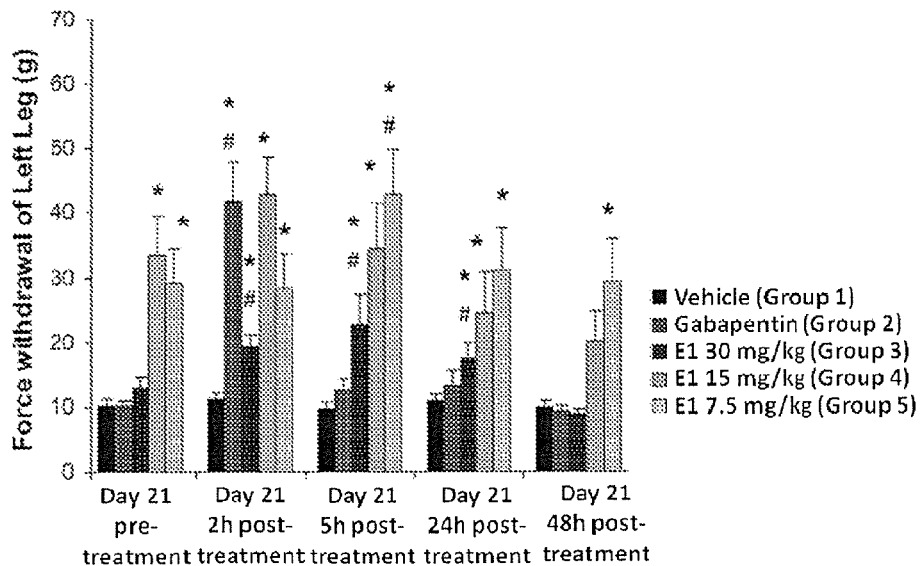
Figure 5A:
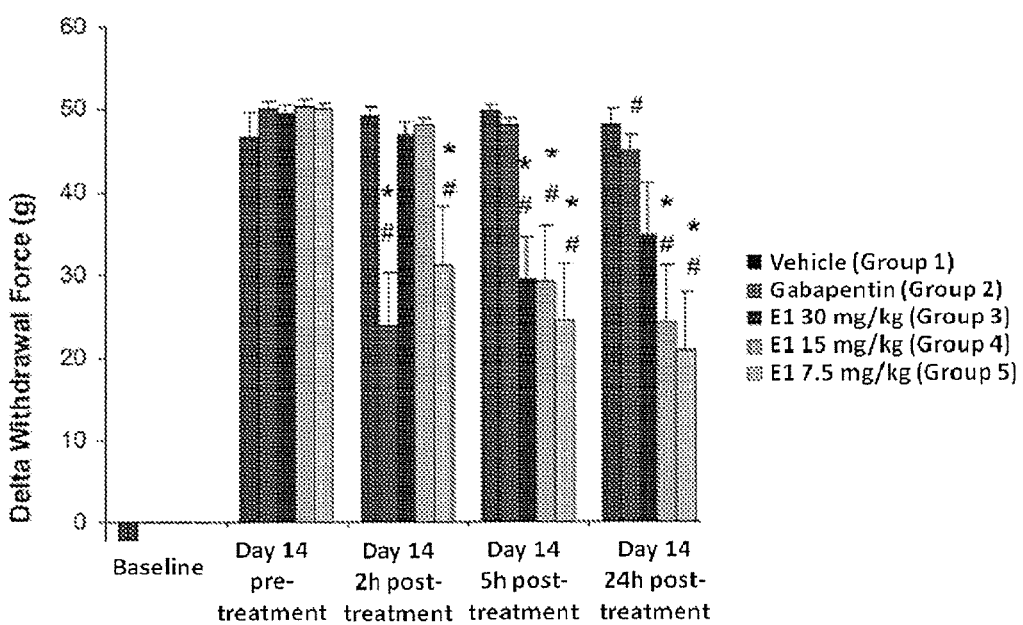

Von Frey Test (Tables 7, 8, 9 and 10; FIGS. 4 and 5): Results were presented as the mean force of withdrawal of left operated leg (g). The mechanical allodynia was observed as an increase in the animal sensitivity to the Von Frey filaments at different time points on study days 14 (2, 5 and 24 hours) and 21 (2, 5, 24 and 48 hours). All values were also calculated and presented as the force needed to withdraw the right healthy leg minus the force needed to withdraw the left operated leg. This calculation presents the values of an animal in a healthy state near 0, thus the withdrawal force for both legs is equal. Animals in a painful state are presented as a larger gap of force between the right healthy leg and the left operated leg. The increase in withdrawal force differences (delta force) presents a more painful state.

Von Frey Response of Test Items Vs. Vehicle: The baseline average force required to withdrawal the left operated leg of istration compared to the Vehicle treated animals: 30.60±5.10 g vs. 10.10±0.60 g in the Vehicle group; $p<0.05$ and also at 24 hours after its administration: 25.20±6.25 g ns vs. 11.80±1.79 g in the Vehicle group; $p=0.05$.

When compared to the Vehicle control treatment with E1 at a dose of 30 mg/kg on study day 21 effectively inhibited allodynia 2 hours after its administration: 19.40±1.80 g vs. 11.40±1.01 g in the Vehicle group $p<0.05$, at 5 hours after its administration: 22.90±4.64 g vs. 9.80±0.90 g in the Vehicle group; $p<0.05$ and also at 24 hours after its administration: 17.50±2.48 g vs. 11.00±1.11 g in the Vehicle group; $p<0.05$.

When compared to the Vehicle control, treatment with E1 at a dose of 30 mg/kg on study day 21 did not inhibit allodynia at 48 hours after its administration: 8.90±0.82 g vs. 9.90±1.21 g in the Vehicle group.

TABLE 7

The mean Von Frey force required for withdrawal of the left operated leg (g): measurements were performed on the $14^{th}$ day of the study:

| Group | | | | Day 14 Post-treatment | | |
|---|---|---|---|---|---|---|
| code | Treatment | Baseline | Day 14 Pretreatment | 2 hours | 5 hours | 24 hours |
| 1 | Vehicle DMSO | 56.60 ± 3.40 | 10.00 ± 0.93 | 10.70 ± 0.98 | 10.10 ± 0.90 | 11.80 ± 1.79 |
| 2 | Gabapentin 150 mg/kg IP | 53.20 ± 4.53 | 10.00 ± 0.88 | 36.30*# ± 6.60 | 11.80 ± 1.85 | 15.20# ± 1.95 |
| 3 | E1 30 mg/kg IP | 60.00 ± 0.00 | 10.50 ± 1.06 | 13.20 ± 1.70 | 30.60*# ± 5.10 | 25.20 ± 6.25 |
| 4 | E1 15 mg/kg IP | 56.60 ± 3.40 | 9.80 ± 0.90 | 11.80 ± 5.67 | 30.80*# ± 6.66 | 35.80*# ± 6.80 |
| 5 | E1 7.5 mg/kg IP | 56.60 ± 3.40 | 9.90 ± 0.64 | 28.80*# ± 7.10 | 32.20*# ± 6.37 | 35.80*# ± 6.80 |

*$p < 0.05$ vs. Vehicle
$p < 0.05$ Pretreatment vs. Post-treatment

E1 15 mg/kg IP (Group 4): When compared to the Vehicle control (Group 1) treatment with E1 at a dose of 15 mg/kg on study day 14 did not inhibit allodynia 2 hours after its administration.

Treatment with E1 at a dose of 15 mg/kg on study day 14 inhibited allodynia 5 and still after 24 hours after its administration compared to the Vehicle treated animals.

When compared to the Vehicle control, treatment with E1 at a dose of 15 mg/kg inhibited allodynia on study day 21 pretreatment; 2, 5 and 24 hours after its administration, however, the treatment with a dose of 15 mg/kg on study day 21 was less effective 48 hours after its administration.

TABLE 8

The mean Von Frey force required for withdrawal of the left operated leg (g): measurements were performed on day 21:

| Group code | Treatment | Day 21 Pretreatment | Day 21 Post-treatment | | | |
|---|---|---|---|---|---|---|
| | | | 2 hours | 5 hours | 24 hours | 48 hours |
| 1 | Vehicle DMSO | 10.10 ± 1.11 | 11.40 ± 1.01 | 9.80 ± 0.90 | 11.00 ± 1.11 | 9.90 ± 1.21 |
| 2 | Gabapentin 150 mg/kg IP | 10.20 ± 0.85 | 41.90*# ± 6.12 | 12.60 ± 1.85 | 13.40 ± 2.29 | 9.50 ± 0.69 |
| 3 | E1 30 mg/kg IP | 13.00 ± 1.76 | 19.40*# ± 1.80 | 22.90*# ± 4.64 | 17.50*# ± 2.48 | 8.90 ± 0.82 |
| 4 | E1 15 mg/kg IP | 33.50* ± 6.04 | 43.00* ± 5.67 | 34.70* ± 7.06 | 24.70* ± 6.17 | 20.20 ± 4.80 |
| 5 | E1 7.5 mg/kg IP | 29.00* ± 5.72 | 28.40* ± 5.52 | 43.10*# ± 6.97 | 31.30* ± 6.50 | 29.30* ± 6.97 |

*p < 0.05 vs. Vehicle
p < 0.05 Pretreatment vs. Post-treatment

E1 7.5 mg/kg IP (Group 5): When compared to the Vehicle control (Group 1), treatment with E1 at a dose of 7.5 mg/kg on study day 14 effectively inhibited allodynia 2, 5 and also 24 hours after its administration.

When compared to the Vehicle control, treatment with E1 at a dose of 7.5 mg/kg inhibited allodynia on study day 21 pretreatment and also 2, 5, 24 and even 48 hours after its administration.

Gabapentin 150 mg/kg IP (Group 2): When compared to the Vehicle control (Group 1), treatment with gabapentin on study day 14 inhibited allodynia 2 hours after its administration; but was not effective 5 hours after its administration.

When compared to the Vehicle control, treatment with gabapentin on study day 21 effectively inhibited allodynia 2 hours after its administration; but was not effective already 5 hours after its administration.

TABLE 9

The difference (delta) force between right healthy leg and left operated leg (g): a 14 day study. Difference is calculated by subtracting the value of force withdrawal of left operated leg from the value of force withdrawal of the right healthy leg.

| Group code | Treatment | Baseline | Day 14 Pretreatment | Day 14 Post-treatment | | |
|---|---|---|---|---|---|---|
| | | | | 2 hours | 5 hours | 24 hours |
| 1 | Vehicle DMSO | −3.40 ± 3.40 | 46.60 ± 3.07 | 49.30 ± 0.98 | 49.90 ± 0.90 | 48.20 ± 1.79 |
| 2 | Gabapentin 150 mg/kg IP | 0.00 ± 0.00 | 50.00 ± 0.88 | 23.70*# ± 6.60 | 48.20 ± 1.85 | 44.80# ± 1.95 |
| 3 | E1 30 mg/kg IP | 0.00 ± 0.00 | 49.50 ± 1.06 | 46.80 ± 1.70 | 29.40*# ± 5.10 | 34.80 ± 6.25 |
| 4 | E1 15 mg/kg IP | 0.00 ± 0.00 | 50.20 ± 0.90 | 48.20 ± 5.67 | 29.20*# ± 6.66 | 24.20*# ± 6.80 |
| 5 | E1 7.5 mg/kg IP | 0.00 ± 0.00 | 50.10 ± 0.64 | 31.20*# ± 7.10 | 24.40*# ± 6.89 | 20.80* ± 7.10 |

*p < 0.05 vs. Vehicle
p < 0.05 Pretreatment vs. Post-treatment

Von Frey Response of Test Items—Post Treatment vs. Pretreatment:

E1 30 mg/kg IP (Group 3): When compared to the pretreatment value, treatment with E1 at a dose of 30 mg/kg on study day 14 inhibited allodynia 5 hours after its administration pre and post treatment. When compared to the pretreatment value, treatment with E1 at a dose of 30 mg/kg on study day 21 inhibited allodynia 2, 5 and even 24 hours after its administration.

Calculation of delta withdrawal force between the two legs showed significant pain relief activity for E1 at a dose of 15 mg/kg on study day 21 pretreatment; 2, 5 and even 24 hours after its administration E1 7.5 mg/kg IP (Group 5): Calculation of delta withdrawal force between the two legs on day 14 showed significant pain relief activity for E1 at a dose of 7.5 mg/kg at 2, 5 and still at 24 hours after its administration.

TABLE 10

The difference (delta) force between right healthy leg and left operated leg (g): a 21 day study. Difference is calculated by subtracting the value of force withdrawal of left operated leg from the value of force withdrawal of the right healthy leg.

| Group code | Treatment | Day 21 Pretreatment | Day 21 Post-treatment | | | |
|---|---|---|---|---|---|---|
| | | | 2 hours | 5 hours | 24 hours | 48 hours |
| 1 | Vehicle DMSO | 49.90 ± 1.11 | 48.60 ± 1.01 | 50.20 ± 0.90 | 49.00 ± 1.11 | 50.10 ± 1.21 |
| 2 | Gabapentin 150 mg/kg IP | 49.80 ± 0.85 | 18.10*# ± 6.12 | 47.40 ± 1.85 | 46.60 ± 2.29 | 50.50 ± 0.69 |
| 3 | E1 30 mg/kg IP | 47.00 ± 1.76 | 40.60*# ± 1.80 | 37.10*# ± 4.64 | 42.50*# ± 2.48 | 51.10 ± 0.82 |
| 4 | E1 15 mg/kg IP | 26.50* ± 6.04 | 17.00* ± 5.67 | 25.30* ± 7.06 | 35.30* ± 6.17 | 39.80 ± 4.80 |
| 5 | E1 7.5 mg/kg IP | 31.00* ± 5.72 | 31.60* ± 5.52 | 16.90*# ± 6.97 | 28.70* ± 6.50 | 30.70* ± 6.97 |

*$p < 0.05$ vs. Vehicle
$p < 0.05$ Pretreatment vs. Post-treatment

E1 15 mg/kg IP (Group 4): When compared to the pretreatment value, treatment with E1 at a dose of 15 mg/kg on study day 14 inhibited allodynia 5 hours and even 24 hours after its administration.

E1 7.5 mg/kg IP (Group 5): When compared to the pretreatment value, treatment with E1 at a dose of 7.5 mg/kg on study day 14 inhibited allodynia 2, 5 and even 24 hours after its administration. When compared to the pretreatment value, treatment with E1 at a dose of 7.5 mg/kg on study day 21 inhibited allodynia 5 hours after its administration.

Gabapentin 150 mg/kg IP (Group 2): When compared to the pretreatment value, treatment with gabapentin on study day 14 inhibited allodynia 2 hours after its administration; but was not effective 24 hours after its administration.

When compared to the pretreatment value, treatment with gabapentin on study day 21 inhibited allodynia 2 hours after its administration.

Delta Withdrawal Force of Test Items Vs. Vehicle:

E1 30 mg/kg IP (Group 3): Calculation of delta withdrawal force between the two legs on day 14 showed significant pain relief activity for E1 at a dose of 30 mg/kg at 5 hours after its administration. Calculation of delta withdrawal force between the two legs on day 21 showed significant pain relief activity for E1 at a dose of 30 mg/kg at 2, 5 and even 24 hours after its administration.

E1 15 mg/kg IP (Group 4): Calculation of delta withdrawal force between the two legs on day 14 showed significant pain relief activity for E1 at a dose of 15 mg/kg at 5 and even 24 hours after its administration: 29.20±6.66 g vs. 49.90±0.60 g in the Vehicle group; p<0.05.

Calculation of delta withdrawal force between the two legs showed significant pain relief activity for E1 at a dose of 7.5 mg/kg on study day 21 pretreatment; 2, 5, 24 and still at 48 hours after its administration.

Gabapentin 150 mg/kg IP (Group 2): Calculation of delta withdrawal force between the two legs on day 14 and on day 21 showed significant pain relief activity for gabapentin at 2 hours after its administration Delta Withdrawal Force of Test Items—Post Treatment Vs. Pretreatment:

E1 30 mg/kg IP (Group 3): When compared to the pretreatment value of delta withdrawal force on day 14, treatment with E1 at a dose of 30 mg/kg inhibited allodynia 5 hours after its administration. When compared to the pretreatment value of delta withdrawal force on day 21, treatment with E1 at a dose of 30 mg/kg inhibited allodynia 2, 5 and 24 hours after its administration.

E1 15 mg/kg IP (Group 4): When compared to the pretreatment value of delta withdrawal force on day 14, treatment with E1 at a dose of 15 mg/kg inhibited allodynia 5 and even 24 hours after its administration.

E1 7.5 mg/kg IP (Group 5): When compared to the pretreatment value of delta withdrawal force on day 14, treatment with E1 at a dose of 7.5 mg/kg inhibited allodynia 2, 5 and 24 hours after its administration.

When compared to the pretreatment value of delta withdrawal force on day 21, treatment with E1 at a dose of 7.5 mg/kg inhibited allodynia 5 hours after its administration.

Gabapentin 150 mg/kg IP (Group 2): When compared to the pretreatment value of delta withdrawal force on day 14, treatment with gabapentin inhibited allodynia 2 hours after its administration however was not effective 5 hours post administration.

When compared to the pretreatment value of delta withdrawal force on day 21, treatment with gabapentin effectively inhibited allodynia 2 hours after its administration.

It is to be noted that treatment with the test compounds as described above, animals treated with E1 laid completely the operated paw on the metal mesh surface of the Von Frey apparatus.

Conclusions:

In view of the findings obtained under the conditions of this study, the E1 at a dose of 30 mg/kg was effective as a pain analgesic item in the spinal nerve ligation model for neuropathic pain in rats as reflected in the parameters of mechanical allodynia at 5 post Test Item administration on study day 14, and at 2, 5 and 24 hours post Test Item administration on study day 21.

E1 at a dose of 15 mg/kg was effective as a pain analgesic item as reflected in the parameters of mechanical allodynia at 5 and 24 hours post Test Item administration on study day 14, and at 2, 5 and 24 hours post Test Item administration on study day 21.

E1 at a dose of 7.5 mg/kg was effective as a pain analgesic item as reflected in the parameters of mechanical allodynia at 2, 5 and 24 hours post Test Item administration on study day 14, and at 2, 5, 24 and 48 hours post Test Item administration on study day 21.

Gabapentin, the positive control in this study, was active at 2 hours after its administration on study days 14 and 21. In contrast to Test Items, the analgesic activity of gabapentin was no longer detected 5 hours, 24 hours and 48 hours post dosing.

Example 5

E1 and E2 Enantiomers Modulate Tyrosine Kinase-Activity

E1 and E2 enantiomers were tested in the BLK, Lyn A, Lyn B and Src (solely E1) kinase assays in a range of 5 concentrations from 1.0 E03 to 1.0 E-05(M). Studies involved the BLK, LynA, LynB, and Src kinase assays. Each compound and concentration was tested in duplicate wells.

This project was completed using the Caliper LabChip 3000 and a 12-sipper LabChip. LabChip assays are separations-based, meaning that the product and substrate are electrophoretically separated, thereby minimizing interferences and yielding the highest data quality available on any screening platform. Z' factors for both the EZ Reader and LC3000 enzymatic assays are routinely in the 0.8 to 0.9 range. The advantages of the LabChip assays include high Z' values, few false positives, few false negatives and analytical quality reproducibility.

The off-chip incubation mobility-shift kinase assay uses a microfluidic chip to measure the conversion of a fluorescent peptide substrate to a phosphorylated product. The reaction mixture, from a microtiter plate well, is introduced through a capillary sipper onto the chip, where the nonphosphorylated substrate and phosphorylated product are separated by electrophoresis and detected via laser-induced fluorescence. The signature of the fluorescence signal over time reveals the extent of the reaction.

The precision of microfluidics allows the detection of subtle interactions between drug candidates and therapeutic targets. The technology is able to detect both strong and weak inhibitors with high accuracy, and routinely identifies drug candidates that conventional techniques miss. Assay conditions are summarized in Table 8:

TABLE 8

Kinase assay conditions

| Kinase | [Enzyme] nM | ATP (@ Km, μM) | Buffer | Detergent | Peptide | Reference inhibitor |
|---|---|---|---|---|---|---|
| BLK | 10.0 | 19.0 | 100 mM Hepes, pH 7.5 | 0.01% Brij-35 | 1.5 μM FL-peptide | Staurosporine |
| Lyn A | 3.5 | 20.0 | | 0.01% Brij-35 | | |
| Lyn B | 15.0 | 10.0 | | 0.01% Brij-35 | | |
| Src | 0.2 | 38.0 | | 0.004% tween 20, 0.003% Brij-35 | | |

Assay Control Data: All assays must pass internal QA/QC standards including a reference 1050 for each assay run which must be within one half log unit (plus or minus) of the accepted historical average. Assay control data are summarized in Table 9:

TABLE 9

Kinase assay control data:

| Kinase tested | Reference compound IC50 (M) | 100% control mean activity % conversion | 100% control STDDEV % conversion | 0% control mean activity % conversion | 0% control STDDEV % conversion |
|---|---|---|---|---|---|
| BLK | 4.87E−09 | 14.25 | 0.18 | 0.59 | 0.32 |
| Lyn A | 3.38E−09 | 37.82 | 0.11 | 0.61 | 0.43 |
| Lyn B | 3.20E−09 | 14.69 | 0.08 | 0.31 | 0.14 |
| Src | 5.88E−09 | 24.64 | 2.94 | 0.49 | 0.28 |

Results: The activity of E1 and E2 enantiomers as modulators of various protein tyrosine kinases is presented Graphically ($IC_{50}$ curves) in FIGS. 6A-D. $IC_{50}$ curves are generated using GraphPad 5 and a standard 4-parameter non linear regression model (log(inhibitor) vs response—variable slope). $EC_{50}$ curves are generated using GraphPad 5 and a standard 4-parameter non linear regression model (sigmoidal dose response—variable slope). Data points are the averages of duplicate wells. Error bars represent the mean±replicate % activity.

It will be appreciated by persons skilled in the art that the present invention is not limited by what has been particularly shown and described herein above. Rather the scope of the invention is defined by the claims that follow.

What is claimed is:

1. A compound having the following formula (II):

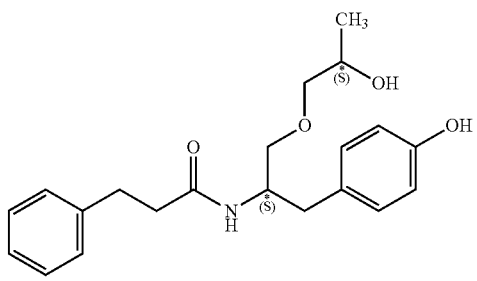

wherein the compound has the specific stereochemistry of (S)2-N(3-O—((S)propan 2-ol)-1-propyl-4-hydroxybenzene)-3-phenylpropylamide or a pharmaceutically acceptable salt or hydrate thereof,
wherein the compound is in a substantially pure form, the compound consisting of at least 90% of (S)2-N(3-O—((S)propan 2-ol)-1-propyl-4-hydroxybenzene)-3-phenylpropylamide and less than 10% of other stereoisomeric forms of the compound.

2. The compound of claim 1, wherein the compound consists of at least 95% of (S)2-N(3-O—((S)propan 2-ol)-1-propyl-4-hydroxybenzene)-3-phenylpropylamide and less than 5% of other stereoisomeric forms of the compound.

3. The compound of claim 1, wherein the compound consists of at least 98% of (S)2-N(3-O—((S)propan 2-ol)-1-propyl-4-hydroxybenzene)-3-phenylpropylamide and less than 2% of other stereoisomeric forms of the compound.

4. A pharmaceutical composition comprising:
a therapeutically effective amount of a compound or a pharmaceutically acceptable salt or hydrate thereof and a pharmaceutically acceptable carrier or diluent, the compound having the following formula (II):

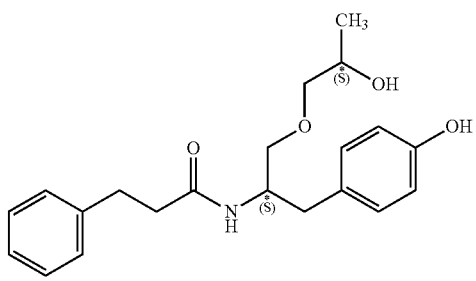

wherein the compound has the specific stereochemistry of (S)2-N(3-O—((S)propan 2-ol)-1-propyl-4-hydroxybenzene)-3-phenylpropylamide or a pharmaceutically acceptable salt or hydrate thereof, wherein the compound is in a substantially pure form, the compound having at least 90% of (S)2-N(3-O—((S)propan 2-ol)-1-propyl-4-hydroxybenzene)-3-phenylpropylamide and less than 10% of other stereoisomeric forms of the compound.

5. The pharmaceutical composition of claim 4, wherein said pharmaceutical composition is formulated as a unit dosage form.

6. The pharmaceutical composition of claim 4, wherein said pharmaceutical composition is formulated for oral administration.

7. The pharmaceutical composition of claim 4, wherein said composition is formulated as a unit dosage form comprising 0.1 mg to about 500 mg of the compound of claim 1 or a pharmaceutically acceptable salt or hydrate thereof.

8. A method for treating or preventing pain in a subject in need thereof, the method comprising administering to said subject a therapeutically effective amount of the compound of claim 1 or a pharmaceutically acceptable salt or hydrate thereof.

9. The method of claim 8, wherein the compound is administered as a pharmaceutical composition comprising a therapeutically effective amount of the compound of claim 1 or pharmaceutically acceptable salt or hydrate thereof, and a pharmaceutically acceptable carrier or diluent.

10. The method of claim 9, wherein the pharmaceutical composition is formulated as a unit dosage form.

11. The method of claim 9, wherein the pharmaceutical composition is formulated for oral administration.

12. The method of claim 9, wherein the composition is formulated as a unit dosage form comprising 0.1 mg to 500 mg of the compound of claim 1 or pharmaceutically acceptable salt or hydrate thereof.

13. The method of claim 9, wherein the pharmaceutical composition is administered as a daily dose of 1.0 mg to 15 g of the compound of claim 1 or pharmaceutically acceptable salt or hydrate thereof.

14. The method of claim 8, wherein the pain is acute or chronic pain.

15. The method of claim 8, wherein the pain is nociceptive pain.

16. The method of claim 8, wherein the pain is neuropathic pain.

17. The method of claim 16, wherein the neuropathic pain is at least one symptom selected from neuropathic pains in post herpetic neuralgia, trigeminal neuralgia, diabetic neuralgia, cancer pain, persistent postoperative or post-traumatic pain, hyperalgia, allodynia, post-thoracotomy pain, CRPS, pain associated with multiple sclerosis, AIDS, thalamic pain, paraplegic pain caused by myelopathy, anesthesia dolorosa and phantom limb pain.

* * * * *